(12) United States Patent
Schwartz et al.

(10) Patent No.: US 10,422,792 B2
(45) Date of Patent: Sep. 24, 2019

(54) BINDING DETECTION USING LIQUID CRYSTAL

(71) Applicants: The Regents of the University of Colorado, a body corporate, Denver, CO (US); Daniel K. Schwartz, Boulder, CO (US); Patrick S. Noonan, Golden, CO (US)

(72) Inventors: Daniel K. Schwartz, Boulder, CO (US); Patrick S. Noonan, Golden, CO (US)

(73) Assignee: THE REGENTS OF THE UNIVERSITY OF COLORADO, Denver, CO (US)

( * ) Notice: Subject to any disclaimer, the term of this patent is extended or adjusted under 35 U.S.C. 154(b) by 0 days.

(21) Appl. No.: 15/121,750

(22) PCT Filed: Mar. 19, 2015

(86) PCT No.: PCT/US2015/021609
§ 371 (c)(1),
(2) Date: Aug. 25, 2016

(87) PCT Pub. No.: WO2015/143247
PCT Pub. Date: Sep. 24, 2015

(65) Prior Publication Data
US 2017/0131266 A1    May 11, 2017

Related U.S. Application Data

(60) Provisional application No. 61/955,592, filed on Mar. 19, 2014.

(51) Int. Cl.
*G01N 33/53* (2006.01)
*C12N 15/115* (2010.01)
*G01N 21/23* (2006.01)

(52) U.S. Cl.
CPC ....... *G01N 33/5308* (2013.01); *C12N 15/115* (2013.01); *G01N 21/23* (2013.01); *G01N 2333/974* (2013.01)

(58) Field of Classification Search
None
See application file for complete search history.

(56) References Cited

U.S. PATENT DOCUMENTS

| 7,947,510 B2 * | 5/2011 | Schwartz | C12Q 1/6825 349/167 |
| 2009/0061527 A1 * | 3/2009 | Schwartz | C12Q 1/6825 436/94 |

FOREIGN PATENT DOCUMENTS

WO    WO-2013065016 A1 *    5/2013   ....... G01N 33/54353

OTHER PUBLICATIONS

Hoppe-Seyler et al (J. Ster. Biochem. Mol. Biol. 78: 105-111, 2001) (Year: 2001).*
Chao et al (Acta Chim. Sinica 2013, 71, 367-370) (Year: 2013).*
Translation of Wu et al (Acta Chimica Sinica 71:367-370, 2013) (Year: 2013).*

* cited by examiner

*Primary Examiner* — Richard A Schnizer
(74) *Attorney, Agent, or Firm* — Don D. Cha; HDC IP Law, LLP

(57) ABSTRACT

The present invention provides methods, devices and kits for detecting binding between two molecules using a liquid crystal.

14 Claims, 10 Drawing Sheets
Specification includes a Sequence Listing.

BINDING DETECTION USING LIQUID CRYSTAL

CROSS-REFERENCE TO RELATED APPLICATIONS

This application claims the priority benefit of U.S. Provisional Application No. 61/955,592, filed Mar. 19, 2014, which is incorporated herein by reference in its entirety.

STATEMENT REGARDING FEDERALLY FUNDED RESEARCH

This invention was made with government support under grant number DMR0820579 awarded by the National Science Foundation. The government has certain rights in the invention.

FIELD OF THE INVENTION

The present invention relates to methods, devices and kits for detecting binding between two molecules using a liquid crystal.

BACKGROUND OF THE INVENTION

Compared to standard methods based on monoclonal antibodies, the development of new aptamers (e.g., using Systematic Evolution of Ligands by Exponential Enrichment [SELEX]) is faster, simpler, more robust, and yields aptamers that can bind selectively and with excellent sensitivity to a wide variety of targets, including small organic molecules, proteins, antibodies, and even cells. Coupled with an appropriate transduction method, aptamers could be the basis of a universal multiplexed detection strategy capable of the simultaneous detection of many different classes of analytes in the same sample.

The advantageous properties of aptamers as a molecular recognition element have inspired the development of biosensors capable of detecting aptamer-ligand binding events. Significant progress has been made in the development of colorimetric, electrochemical, fluorescence, and mass-sensitive strategies. However, these detection methods are fundamentally limited for multiplexed applications. When aptamer-ligand binding occurs in the bulk phase (e.g., as used in nanoparticle colorimetric and label-free fluorescence assays) a characteristic detection signal for each target species is required (e.g., fluorescence emission wavelength), placing a finite constraint on multiplexing capacity. Other strategies, such as mass-sensitive and electrochemical detection, confine the aptamer-ligand binding to an interface and thus have the potential for site-dependent multiplexing. Unfortunately, signal transduction in many of these approaches is highly non-specific (e.g., surface adsorption or localization of redox species) and the presence of even small amounts of interfering species will produce a false response.

Accordingly, there is a need for a universally multiplexed aptasensor. In particular, the transduction element should ideally be label-free and respond specifically to aptamer-ligand binding.

Another area of current interest is understanding how to control bilayer fusion. Such an understanding is fundamentally and technologically important for designing synthetic gene transfer agents, drug delivery strategies, studying biological systems, and developing diagnostic assays. In particular, in vivo biomimetic strategies for studying receptor-mediated fusion have played a major role in the advancement of this field. Since Rothman and coworkers first demonstrated that SNARE proteins were the minimum machinery required for inducing membrane fusion, they have been widely accepted as the most efficient fusogenic receptors. Their biological origin and prevalence in cellular membranes have inspired exploration of the mechanisms that allow SNARE proteins to work with such high efficacy. A common motif has been found among SNARE receptors that involve a bundle of four alpha-helices that associate upon recognition. The configuration of this quaternary structure induced strain to the associated lipid bilayers, initiating the fusogenic process. Several synthetic approaches that mimic this structural motif have been developed using peptides, model proteins, small molecules, and DNA in an effort to achieve efficient recognition, bilayer disruption, and content transport in vivo.

In particular, DNA hybridization mediated fusion shows promise as a reductionist system both for studying fusion mechanics and as a bio-sensing strategy. Studies have shown that DNA can be anchored to lipid bilayers using DNA-lipid conjugates or sterol tethered DNA. Unilamellar liposomes can therefore be prepared with such tethered oligonucleotides. When two liposomes prepared with different but complementary oligonucleotides were combined, lipid mixing assays revealed bilayer fusion. A critical requirement in these assays was that membrane anchors on complementary DNA strands were necessarily on opposite ends of the DNA (i.e. 5' and 3' ends). In this configuration, DNA hybridization mimicked the configuration of the four helix bundle in SNARE receptors, brought the two bilayers into close proximity, strained the bilayer structure, and consequently induced efficient lipid mixing and content transport. In the alternative situation where the tethers were on the same end of the DNA, the liposomes were observed to aggregate but no lipid mixing or content transport occurred, presumably due to a lack of bilayer-bilayer proximity and strain.

Studying receptor-mediated fusion in dispersed liposomes is convenient for proof-of-concept studies but has limited capacity for advancing related technologies. Alternatively, receptor-mediated fusion with planar interfaces, and in particular supported lipid bilayers, has been used for quantitative high throughput studies that elucidate cellular mechanisms related to drug discovery, medical diagnostics, and biosensor development. Supported lipid bilayers can be fabricated as spatially addressed microarrays capable of high throughput screening and have demonstrated value as a tool for studying a range of biochemical processes. Despite their success as model systems, supported lipid bilayers possess complicating factors such as interfering effects associated with the underlying solid substrate and the necessity of complex and expensive analytical instrumentation. Thus, substrates that address some of these drawbacks have significant value toward a better understanding of liposome fusion from a fundamental and technological perspective.

SUMMARY OF THE INVENTION

One aspect of the invention provides a method for determining the occurrence of hybridization or formation of hybridization of oligonucleotides. Such a method typically comprises: contacting a sample fluid to a liquid crystal (LC)-solvent interfacial layer, wherein said LC-solvent interface comprises a lipid or surfactant and a selection oligonucleotide that is fused, i.e., embedded or anchored, within a lipid layer of said LC-solvent interface. One end of the selection oligonucleotide may be modified as to allow the selection oligonucleotide to be bound within the lipid layer. In one embodiment, the selection oligonucleotide may comprise an aptamer that binds selectively to a ligand of interest that is present within the sample, causing a reorientation of the liquid crystal, thereby allowing one to detect the presence of the ligand.

In another embodiment, the sample, typically a fluid or liquid, may comprise liposomes comprising an oligonucleotide that is complementary to the selection oligonucleotide within said liposome structure. In this case, as with the selection oligonucleotide, one end (often the opposite end compared to the selection oligonucleotide) of the liposome oligonucleotide may also modified to allow it to be held within the liposome structure. When hybridization occurs, orientation of the liquid crystal changes thereby allowing one to detect hybridization and/or fusion of liposome to the lipid.

In one embodiment, one of the oligonucleotides further comprises a partially hybridized aptamer that is capable of being selectively bound to a ligand when said ligand is present. Typically, the aptamer has a higher binding affinity to said ligand than said oligonucleotide, thereby allowing the aptamer to be released from the oligonucleotide.

By detecting the change in orientation of the liquid crystal, one can determine the presence of the ligand or hybridization of oligonucleotides or fusion of liposomes.

The terms "nucleic acid" "polynucleotide" and "oligonucleotide" are used interchangeably herein and refer to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Another aspect of the invention provides a method for determining the presence of a ligand that is not labeled in a sample fluid, said method comprising: (a) contacting said sample fluid with a surfactant-aptamer interfacial layer under conditions sufficient to form an aptamer-ligand complex when said ligand is present in said sample fluid, wherein said surfactant-aptamer interfacial layer is present at a liquid crystal and a polar solvent interface, and wherein said aptamer is capable of selectively binding to said ligand, and wherein said aptamer-ligand complex changes orientation of said liquid crystal compared to the orientation of said liquid-crystal in the absence of said aptamer-ligand complex; and (b) detecting the orientation of said liquid crystal, wherein detection of change in orientation of said liquid crystal indicates the presence of said ligand in said sample fluid.

In some embodiments, said surfactant comprises a cationic surfactant. In some instances, said cationic surfactant comprises a monoalkylquaternary ammonium surfactant, dialkylquaternary ammonium surfactant, trialkylquaternary ammonium surfactant, a monoalkylpyridinium surfactants, quaternized polyoxyethylenated long chain amines, or a combination thereof.

Yet in other embodiments, said surfactant further comprises a nonionic surfactant. In some instances, said nonionic surfactant comprises alkylpolyoxyethylene (e.g. Brij) surfactants, polyoxyethylenated polyoxypropylene (e.g. poloxamer), sorbitan alkyl ester (Span), polyoxyethylene glycol sorbitan alkyl ester (Tween or polysorbate) surfactants, or a mixture thereof.

Still in other embodiments, said liquid crystal is a thermotropic liquid crystal. In some instances, said liquid crystal comprises (4-cyano-4'-pentylbiphenyl), (4-cyano-4'-pentyl-p-terphenyl), (N-(4-methoxybenzylidene-4'-butylaniline), 4'-di-n-hexyldiphenyldiacetylene, other biphenyl or terphenyl liquid crystal compounds, or a mixture thereof.

Often said polar solvent comprises an aqueous solution.

Yet in other embodiments, said step of detecting orientation of said liquid crystal comprises detecting a change in the birefringence of said liquid crystal. Still in other embodiments, a polarized light is used to detect orientation of said liquid crystal. In other embodiments, a light microscopy is used to detect orientation of said liquid crystal.

Still another aspect of the invention provides a method for detecting the presence of a non-labeled ligand in a sample using a non-labeled aptamer, said method comprising: (i) placing said sample on a ligand detection apparatus comprising a liquid crystal and a non-labeled aptamer that bounds selectively to said ligand, wherein said aptamer changes conformation upon binding to said ligand, and wherein the orientation of said liquid crystal changes depending on the conformation of said aptamer; and (ii) detecting the change in orientation of said liquid crystal to determine the presence of said ligand in said sample.

In some embodiments, said ligand detection apparatus further comprises a solid substrate, and wherein said liquid crystal is bound to said solid substrate. Still in other embodiments, said ligand detection apparatus further comprises a surfactant and a polar solvent such that a surfactant-aptamer interfacial layer is present at the interface of said liquid crystal and said polar solvent. Yet in other embodiments, said method of detecting the change in orientation of said liquid crystal comprises determining a change in birefringence of said liquid crystal.

Still another aspect of the invention provides an assay kit for analyzing the presence of a ligand in a sample, said assay kit comprising: (i) a solid substrate; (ii) a liquid crystal that is bound to said solid substrate; (iii) a surfactant; and (iv) an aptamer that is capable of selectively bind to a ligand to form a ligand-aptamer complex when said ligand is present in a sample to be tested, wherein said assay kit is configured to have a different birefringence of said liquid crystal in the presence of said ligand-aptamer complex compared to birefringence of said liquid crystal in the absence of said ligand-aptamer complex.

In some embodiments, said aptamer is selective for a protein or a small molecule.

DETAILED DESCRIPTION OF THE INVENTION

Figure 1:
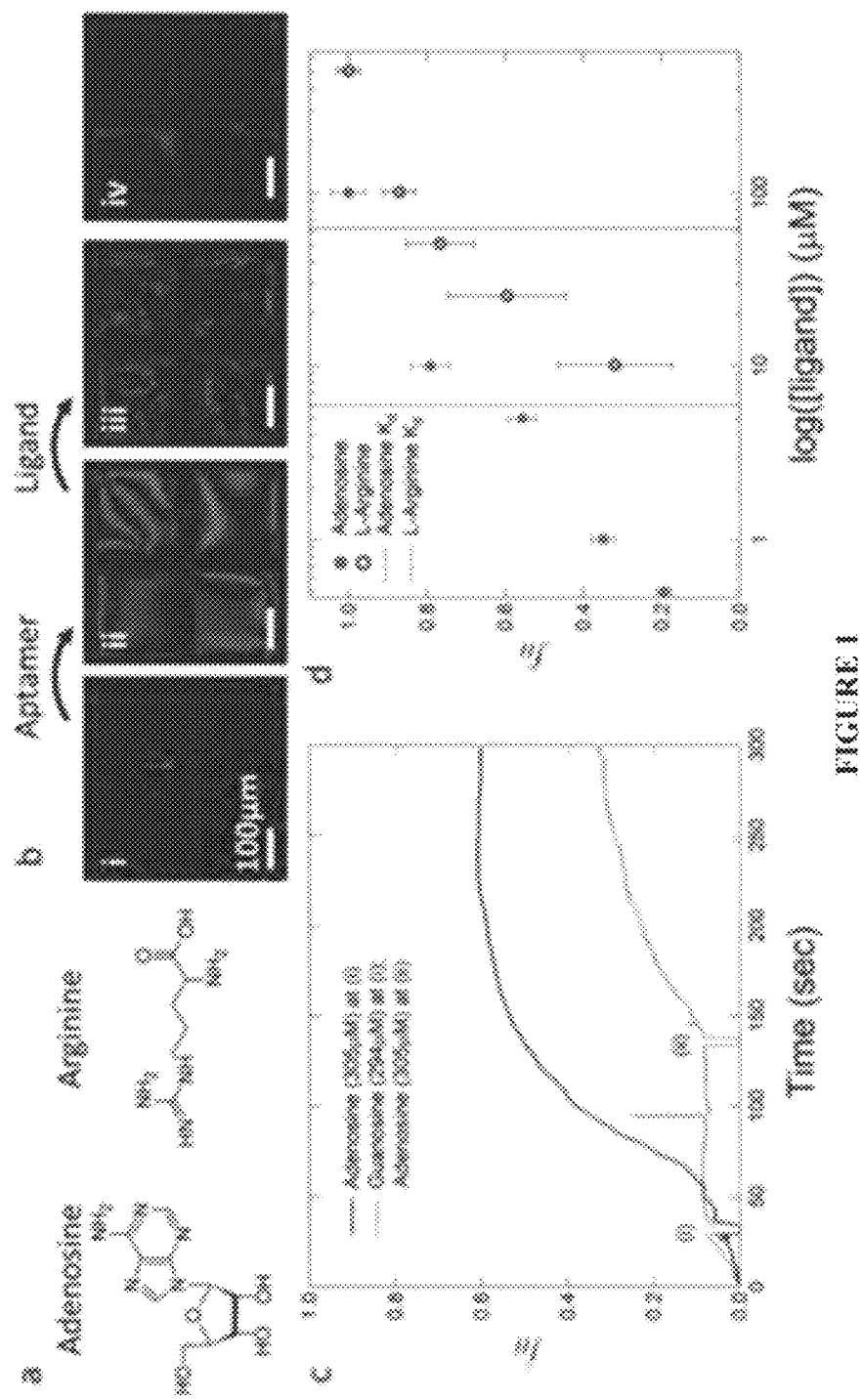
FIG. 1 show chemical structure of the aptamer targets (panel "a"); polarized light microscopy images of the aqueous/LC interface (panel "b" where (i) is image laden with OTAB, (ii) is an image after adsorption of the adenosine aptamer (2.5 µM), (iii) is an image about 20 sec after addition of adenosine (=300 µM), and (iv) is an image about 5 min after addition of adenosine; dynamic LC response upon addition of ligands: $f_H$=fractional increase in homeotropic area (panel "c"); and upon subsequent additions of either adenosine or arginine (panel "d").

Liquid crystal (LC)-based sensing schemes have proven capable of specific signal transduction through LC reorientations driven by interfacial enzymatic reactions or molecular binding events. The unique interfacial phenomena that lead to LC reorientation in these systems are complex and subtle, often involving the competition between multiple non-covalent intermolecular interactions. Furthermore, the intrinsic cooperative behavior associated with the long-range orientational order of the LC phase provides a natural amplification effect, eliminating the need for (bio)chemical amplification, labeling, and/or expensive instrumentation.

Some aspects of the invention provide a LC-based detection of aptamer binding in a label-free multiplexed un-amplified detection of various ligands including, but not limited to, small organic molecules, nucleic acids, proteins such as antibodies and receptors, and even cells. As used herein, the term "small organic molecules" refers to an organic compound having a molecular weight of about 1000 g/mole or less, typically about 600 g/mole or less, and often 400 g/mole and less. Exemplary small organic molecules include non-protein or nucleic acid based drugs that are known to one skilled in the art. Exemplary drugs include antibiotics, anti-inflammatories, analgesics, antiviral compounds, antifungal compounds, CNS suppressants and stimulants, antipsychotics, antidepressants, as well as other drugs known to one skilled in the art. See, for example, Physician's Desk Reference, 2013. The simultaneous detection of multiple molecular species in a label-free sensor scheme is useful in a wide variety of applications including, but not limited to, environmental monitoring, bio/chemical warfare detection, medical diagnostics, drug detections, criminal investigations, as well as other known applications for a diagnostic system.

The extraordinary physical properties of liquid crystal (LC) materials—long-range orientational order, responsiveness to external stimuli, and optical anisotropy—have made them uniquely valuable in display and optoelectronic applications. These same properties have been used in other applications where chemical signals can be converted into simple visual cues. Accordingly, some aspects of the invention are based on the discovery by the present inventors of a dynamic LC response to specific binding events associated with selective molecular recognition by aptamers. Aptamers are nucleic acid constructs that can be engineered to recognize a diverse range of targets such as, but not limited to, small organic molecules, nucleic acids, proteins such as antibodies and receptors, and even cells. It has been discovered by the present inventors that the LC is influenced by the conformational change of the aptamer's secondary structure that occurs upon target binding (i.e., selective binding to a ligand).

As stated above, liquid crystals, in particular thermotropic LCs, have demonstrated utility in the transduction of molecular events at an interface into macroscopic responses visible with the naked eye. The orientation of LC molecules is extraordinarily sensitive to physical and chemical properties of a bounding interface, and the long-range order inherent in LC phases serves to amplify surface-induced ordering for macroscopic distances. These properties, combined with the optical anisotropy of LC molecules make them well-suited for the direct transduction and amplification of the binding of an analyte to a target at an interface into an optical output. Unlike most current methods for the detection of biological analytes, which generally require laboratory-based analytical detectors and labeled species such as fluorophores or radioactive isotopes, LC-based detection can be carried out in ambient light without the need for electrical power or molecular labels, e.g., fluorescence, isotope, etc. This makes LC-based detection particularly useful for detection assays performed away from central laboratory locations including point-of-care, home-based, and field-based assays.

Some embodiments of LC-based detection rely on optical, anchoring, and elastic properties arising from molecular anisotropies and the unique liquid-crystalline phase of the LC material. The molecular anisotropy of a liquid crystalline sample creates a difference in the refractive indices of light parallel and perpendicular to the bulk molecular orientation, i.e., the LC director. This difference, known as birefringence, creates a discernable optical signal that is lost when the director orients parallel to the direction of light propagation. Molecular-scale interactions between a LC and a neighboring interface result in a preferred anchoring angle relative to the surface normal. It is believed that information about the interface, in the form of surface anchoring, is transmitted as far as 100 μm into the bulk as a result of the elastic nature of the LC director field.

It has previously been shown that coupling the structure of the interface to a bioreaction, such as molecular recognition, in some instances cause a bulk reorientation of the LCs as the reaction proceeds, generating an optical signal. The aqueous/LC interface is particularly useful in this regard, because the aqueous phase permits convenient molecular transport to the interface and the fluidity of the interface allows for large-scale molecular re-arrangements. Furthermore, the chemical properties of the interface can be modified in a controlled way by adsorption of a surfactant monolayer. In some instances, in the absence of surfactant, a highly tilted (nearly planar) LC orientation is observed. At sufficient surfactant coverage, the tilted anchoring at the interface reorients to a homeotropic alignment. The present inventors have previously discovered that long-chain n-alkanoic acids adsorbed at the aqueous/LC interface possess distinct 2D phases dependent on the surfactant chemical potential and the temperature of the interface. These phases are also characterized by molecular packing density, tilt, and lateral organization. LC anchoring is sensitive to these structural details.

In one aspect, the present invention provides a method of detecting the presence of a ligand in a sample fluid. The method includes contacting a sample fluid with a surfactant-aptamer interfacial layer, where in some embodiments the surfactant comprises a cationic surfactant and optionally a nonionic surfactant. The term "optionally" means the nonionic (e.g., neutral) surfactant may or may not be present. It should be noted, however, regardless the presence or absence of the nonionic surfactant, the surfactant always includes a cationic surfactant. Typically, the cationic surfactant comprises at least 50% of the total amount of surfactant. Alternatively, if and when nonionic surfactant is present, it is typically present at the amount of about 25% or less, and often about 10% or less of the total amount of the surfactant. The surfactant-aptamer interfacial layer comprises a surfactant and a probe aptamer. The surfactant-aptamer interfacial layer is present at the interface of a liquid crystal and a polar solvent. The sample fluid is contacted with this surfactant-aptamer interfacial layer under conditions sufficient to form an aptamer-ligand binding complex (or simply aptamer-ligand complex) when the ligand is present in the sample fluid. It should be noted that the aptamer selectively binds the ligand such that the selectivity of the aptamer for the ligand is at least 60%, typically at least 80%, and often at least 99%. When the aptamer-ligand binding complex is formed, it reorients the liquid crystal (e.g., from tilted to homeotropic or vice-versa). This reorienting of LC can be readily detected by any of the currently available methods including a simply visual observation, thereby providing detection of the presence (or absence) of aptamer-ligand binding complex. The surfactant-aptamer interfacial layer can be formed, e.g., by combining a surfactant, a liquid crystal and an aptamer dissolved in a polar solvent.

The sample fluid and the aptamer are typically dissolved in a polar solvent. Exemplary polar solvents include, but are not limited to, an aqueous solution (e.g., water), a lower chain (e.g., $C_1$-$C_4$) alcohol, nitriles, amides, carboxylic acids, and other polar solvents having a dielectric constant of about 15 or more, typically about 25 or more, and often 40 or more. In some embodiments, the sample fluid is exposed to the liquid crystal. Yet in other embodiments, the liquid crystal contains the surfactant at the time the sample fluid contacts the liquid crystal. In other embodiments, the surfactant is dissolved in the polar solvent with aptamer prior to contacting the liquid crystal with the polar solvent. And in still other embodiments, the surfactant is added to an interface formed between the polar solvent and the liquid crystal.

Suitable aptamers can be readily prepared by one skilled in the art. For example, U.S. Pat. No. 5,637,459, issued on Jun. 10, 1997 to Burke et al., which is incorporated herein by reference in its entirety, discloses what is commonly known in the art as the SELEX process for preparing aptamers for a particular ligand.

Still in other embodiments, the sample fluid and a solution comprising the aptamer is first combined under conditions sufficient to form the aptamer-ligand binding complex, if the ligand is present in the sample fluid to form an analyte solution. This analyte solution is then contacted with the liquid crystal that comprises a surfactant-polar solvent interface as described herein. In some instances within these embodiments, one can determine the presence or absence of the aptamer-ligand binding complex by comparing the LC orientation with that of the aptamer in the same condition, except for the presence of the aptamer-ligand binding complex. This latter mixture can serve as a "negative control", i.e., absence of aptamer-ligand binding complex. By comparing this negative control with that of the LC in the sample fluid, one can determine whether any aptamer-ligand is present in the sample fluid.

Without being bound by any particular theory, it is believed that the surfactant forms a surfactant layer (e.g., a cationic surfactant monolayer) at the interface between the liquid crystal and the polar solvent, and that the aptamer disrupts this surfactant monolayer on the interface between the LC and the polar solvent. The surfactant monolayer may interact with (or complex with) the aptamer through its cationic head groups. It is believed that the aptamer-ligand complex interacts differently with the surfactant monolayer than does the aptamer alone.

Formation of the surfactant-aptamer interfacial layer is believed to be a relatively spontaneous reaction, which occurs when a surfactant and aptamer are combined with the liquid crystal and the polar solvent (such as water). In some embodiments, the cationic surfactant comprises a monoalkyl quaternary ammonium salt surfactant, a dialkyl quaternary ammonium salt surfactant, a trialkyl quaternary ammonium salt surfactant, a monoalkylpyridinium salt surfactant, or a combination thereof. Examples of monoalkyl quaternary ammonium salt surfactants include monoalkyl quaternary ammonium bromide and chloride salts such as dodecyltrimethylammonium bromide, dodecyltrimethylammonium chloride, tetradecyltrimethylammonium bromide, tetradecyltrimethylammonium chloride, hexadecyltrimethylammonium bromide, or hexadecyltrimethylammonium chloride. In one particular embodiment, the monoalkyl quaternary ammonium salt surfactant is octadecyltrimethylammonium bromide (OTAB).

In other embodiments, the cationic surfactant is a dialkyl quaternary ammonium surfactant, such as dioctadecyldimethylammonium bromide. The cationic surfactant can also be a trialkyl quaternary ammonium salt surfactant such as trioctadecylmethylammonium bromide. In one particular instance, the cationic surfactant is a monoalkylpyridinium salt surfactant, such as hexadecylpyridinium bromide. It should be appreciated regardless which cationic surfactant is used, nonionic surfactant can optionally be present as disclosed herein.

As stated herein, in some embodiments the surfactant layer can also include nonionic surfactant. Suitable nonionic surfactants will be known readily by one skilled in the art having read the present disclosure. Exemplary nonionic surfactants that are useful in the present invention include, but are not limited to, alkylpolyoxyethylene (e.g. Brij) surfactants, polyoxyethylenated polyoxypropylene (e.g. poloxamer), sorbitan alkyl ester (Span), polyoxyethylene glycol sorbitan alkyl ester (Tween or polysorbate) surfactants, and a combination thereof. When used, the amount of nonionic surfactants is about 50% or less, typically about 25% or less, and often about 10% or less of the total amount of the surfactant.

The surfactant can be dissolved in a liquid crystal and contacted with a polar solvent. The polar solvent can comprise the aptamer or the aptamer can be added after addition of the surfactant. Regardless of the order of addition, in some embodiments a surfactant-aptamer interfacial layer at the liquid crystal/polar solvent interface is formed. Typically, the surfactant and the aptamer form a non-covalent surfactant-aptamer complex. In some embodiments, the surfactant-aptamer interfacial layer is contacted with a sample fluid under conditions sufficient to form an aptamer-ligand complex, if ligand is present in the sample fluid, within the surfactant-aptamer interfacial layer. Binding of the aptamer and the ligand induces a reorientation of the liquid crystal which is detectable and indicative of the presence of the aptamer-ligand binding complex.

Aptamers that are suitable for methods of the invention can be produced by SELEX or other similar processes that are known to one skilled in the art. In some embodiments, the aptamer is typically 15 to 100 nucleobases in length. In other embodiments, the aptamer is 10 to 200 nucleobases long. It should be appreciated that selectivity of the aptamer for a particular ligand of interest can be readily determined by one skilled in the art during the aptamer production process.

In some embodiments, the liquid crystal is a thermotropic liquid crystal, a polymeric liquid crystals, nematic liquid crystal, smectic liquid crystal, columnar liquid crystal, nematic discotic liquid crystal, calamitic liquid crystal, ferroelectric liquid crystal, discoid liquid crystal, cholesteric liquid crystal or mixtures thereof. In certain embodiments, the liquid crystal is a thermotropic liquid crystals. The thermotropic liquid crystal can include (4-cyano-4'-pentylbiphenyl) ("5CB") or other cyanobiphenyls, (4-cyano-4'-pentyl-p-terphenyl) ("5 CT") or other cyanoterphenyls, (N-(4-methoxybenzylidene-4'-butylaniline) ("MBBA"), 4,4'-di-n-hexyldiphenyldiacetylene, E7 liquid crystal, or a mixture thereof. In one particular embodiment, the liquid crystal is E7. The liquid crystal is typically hydrophobic and therefore capable of forming a layer separated from a polar solvent. Thus, in some embodiments, the liquid crystal is a liquid crystal layer. The surfactant-aptamer interfacial layer can form on top of the liquid crystal layer. It is believed that the polar solvent layer is typically separated from the liquid crystal layer by the surfactant-aptamer interfacial layer.

In some embodiments, the reorientation of the liquid crystal is detected by measuring changes in the birefringence of the liquid crystal. Without being bound by any theory, it is believed that the interaction between the interfacial aptamer and the ligand at the interface between liquid crystal and polar solvent induces a change in the interfacial structure of the surfactant-aptamer interfacial layer which then causes a reorientation of the liquid crystal. The reorientation of the liquid crystal changes the direction of the birefringent optical axes of the liquid crystal relative to the direction of the propagation of light through the device. This changes the effective birefringence of the device and creates a discernable optical signal.

The reorientation and birefringence of the liquid crystal described herein can be monitored using any appropriate technique known to those of skill in the art, such as polarized light microscopy or by simply visualizing the LC without the aid of any detecting device. Liquid crystal orientation and textures can be observed with a light microscope that has been modified for transmission mode incorporating crossed polarizers. In some embodiments, the changes in birefringence are detected with the naked eye using a light source and two polarizers, such as in a passive LCD display.

In other embodiments, the reorientation of LC can be detected by detecting changes to the optical texture of the liquid crystal upon formation of the aptamer-ligand binding complex.

In some embodiments, the methods can be used to determine the formation of a plurality of aptamer-ligand binding complexes using a plurality of different aptamers and a plurality of different ligands. Thus, the methods of the present invention can include more than one aptamer and/or more than one ligand.

In another aspect, the invention provides a device to detect the presence of a ligand in a sample fluid. The device includes a solid substrate, a liquid crystal on the solid substrate, a polar solvent, and a surfactant-aptamer interfacial layer as described herein. It should be appreciated that the surfactant-aptamer interfacial layer can be formed any time prior to its actual use. The solid substrate functions to support the liquid crystal and/or the polar solvent depending upon the particular orientation as described in the methods disclosed herein. The surfactant-aptamer interfacial layer comprises a surfactant and an aptamer having selectivity for a particular ligand of interest. The surfactant-aptamer interfacial layer is typically present at the interface of the liquid crystal and the polar solvent. The solid substrate is typically selected to be non-reactive with the liquid crystal, the surfactant, and/or the aptamers. The solid substrate is also typically substantially planar to provide a surface support for the liquid crystal.

In some embodiments, the device is in the form of a multiplex device in an array format such as a biochip. The multiplex device can include a plurality of discrete liquid crystal volumes (e.g. in the form of thin layers) separated or compartmentalized in an array format, in which each liquid crystal compartment includes a surfactant-aptamer interfacial layer and a different aptamer. Thus, the multiplex device is capable of simultaneously forming a binding complex of a plurality of different ligands to a plurality of different aptamers.

In another aspect, the invention provides a kit to detect aptamer-ligand binding complex. The kit includes a liquid crystal, and a surfactant as described herein, and an aptamer that is typically dissolved in a polar solvent. The kit can also include a solid substrate (e.g. a biochip) and/or a sample ligand.

In another aspect, the invention provides a surfactant-aptamer interfacial layer formed by combining a surfactant, a liquid crystal, and an aptamer in a polar solvent. In another aspect, the invention provides a surfactant-aptamer interfacial layer. The surfactant-aptamer interfacial layer comprises a surfactant and an aptamer. The surfactant-aptamer interfacial layer is typically present at the interface of (e.g., between) the liquid crystal and the polar solvent.

The elements of the methods disclosed herein are equally applicable, where appropriate, to the disclosed compositions and devices. For example, the characteristics of the surfactant-aptamer interfacial layer described in the description of the methods herein are equally applicable to the surfactant-aptamer interfacial layer referred to in the description of the devices, kits, and compositions.

Another aspect of the invention provides a method for detecting oligonucleotide hybridization-mediated liposome fusion. One particular embodiment of this aspect of the invention provides a method for determining hybridization of oligonucleotides within a liposome and/or the presence of a hybridizable complementary oligonucleotide within a liposome. Such a method typically includes contacting a sample fluid comprising a liposome with a liquid crystal. The liquid crystal is bound to a solid substrate such as silica oxide, glass, plastic or other suitable non-reactive, typically transparent solid material. As used herein, the term "non-reactive" means the solid substrate does not undergo chemical reaction with any of the materials including LC, oligonucleotides, liposomes, lipids, and other materials present in the detection system. The liposome comprises an "embedded" or anchored oligonucleotide, which is referred to herein as "liposome oligonucleotide".

The liquid crystal-solvent interfacial layer includes a layer of lipid in which oligonucleotides (referred to herein as "selection oligonucleotides") is embedded or anchored therein. When the selection oligonucleotides and the liposome oligonucleotides are sufficiently complementary, they hybridize to form a double stranded oligonucleotide (or "DS oligonucleotide"). It should be appreciated that one or both of the liposome oligonucleotide and selection oligonucleotide can be double stranded. In such cases, the "DS oligonucleotide" is actually not a double strand but triple or quadruple oligonucleotide strands.

As stated, the liquid crystal-solvent interfacial layer comprises a lipid and a modified oligonucleotide that are fused (i.e., embedded or anchored) within the LC-solvent interface. The sample fluid typically comprises a liposome comprising a liposome oligonucleotide that is (e.g., embedded or anchored) within the liposome structure. It should be appreciated that the liposome oligonucleotide is also typically modified (for example, attached to a cholesterol) to allow it to be embedded or anchored or placed within the liposome structure. For example, the liposome oligonucleotide is attached to cholesterol or other compounds that can be used to "embed" or "anchor" the oligonucleotide to the liposome structure. Suitable anchoring molecules are well known to one skilled in the art. It should be appreciated that the selection oligonucleotide is similarly attached to a molecule that allows it to be fused within the lipid structure.

When the liposome oligonucleotide and the selection oligonucleotide are sufficiently complementary (e.g., at least about 90%, typically at least about 95%, often at least about 98%, and most often 100%) to form a stable hybridized DS oligonucleotide, hybridization can be detected by change in birefringence of the liquid crystal. The term "about" refers to ±20%, typically ±10%, and often ±5% of the numeric value. In some embodiments, the liposome oligonucleotide or the selection oligonucleotide can include a partially hybridized aptamer that is capable of being selectively bound to a ligand. Thus, when a suitable ligand is present the aptamer portion of will bind to the ligand causing its release from the oligonucleotide. This occurs when the aptamer has a higher binding affinity towards the ligand than to the oligonucleotide. In the latter instances, change in orientation of the liquid crystal indicates the presence of the ligand in the mixture, typically in the sample fluid that is analyzed.

The method of the invention can also include the steps of preparing said LC-solvent interface. Typically, the LC-solvent interface preparation step comprises contacting the LC-solvent interface with a solution comprising a micelle that includes the lipid and the selection oligonucleotide within the structure of the micelle under condition sufficient to produce the LC-solvent interface with the selection oligonucleotide that is fused within the lipid layer of the LC-solvent interface.

It should be appreciated that since the methods of the invention detects hybridization between the liposome oligonucleotide and the selection oligonucleotide, one of the oligonucleotide is modified at the 3'-end and the other is modified at the 5'-end.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1: Methods

Preparation of self-assembled monolayers (SAMs) of octadecyltriethoxysilane (OTES) (Gelest Inc.) was carried out according to the procedure described by Walba, D. M. et al., in Liquid Crystals, 2004, 31(4), 481-489. Briefly, soda lime glass microscope slides (Corning Inc.) were cleaned sequentially with 2% aqueous micro-90, deionized water (18.2 Me), and piranha solution (30% aqueous $H_2O_2$ (Fisher Scientific) and concentrated $H_2SO_4$ (Fisher Scientific) 1:3 (v/v) at ~80° C. for 1 hr. Following piranha cleaning, microscope slides were rinsed with deionized water (18.2 Me) and dried under a stream of ultrapure $N_2$. A deposition solution of n-butylamine (Fisher Scientific) and OTES was prepared in toluene (Fisher Scientific) at 1:3:200 volumetric ratios, respectively, and warmed to 60° C. The clean and dry microscope slides were then rinsed with toluene, submerged in the warm deposition solution, and incubated for 1 hour at 60° C. Upon removal from the deposition solution, the slides were rinsed with toluene, dried under a stream of ultrapure $N_2$, and stored at room temperature in a vacuum desiccator. A custom-built contact angle goniometer was used to verify that the water contact angle ($\theta_C$, measured via the static sessile drop method) of the prepared SAMs was sufficient to indicate strong homeotropic anchoring ($\theta_C > 95°$).

OTAB (Sigma-Aldrich) laden LC films were prepared by housing the nematic E7 LC (Merck KGaA) within the pores of an electron microscopy grid (Electron Microscopy Sciences) placed onto a solid glass substrate functionalized with an octadecyltriethoxysilane self-assembled monolayer (SAM). The SAM maintained homeotropic orientation of the LC at the solid substrate. The grids were contained within silicone isolators (Grace-bio Labs, #664206) placed onto SAM-functionalized glass. A solution of OTAB in E7 was prepared at [OTAB]-100 µM. The pores of the electron microscopy grid were then filled with the LC/OTAB mixture by pipetting ~250 nL into the grid and removing the excess via capillary action. Next, the wells were filled with ~25 µL of an aqueous solution (2.5 mM $Na_2PO_4H$; Sigma Aldrich). The ssDNA adenosine selective aptamer (or "adenosine aptamer" as sometimes referred to herein) (5'-AC-CTGGGGGAGTATTGCGGAGGAAGGT-3' (SEQ ID NO:1); Invitrogen), a ssDNA mismatch adenosine aptamer (i.e., ssDNA that has the same sequence as the adenosine selective aptamer but has one or more nucleobases that has been substituted with a different nucleobase) (5'-AC-CTGGGGGAGTATTGCGGAGCAAGGT-3' (SEQ ID NO:2); Invitrogen), or the ssRNA arginine aptamer (also referred to herein as "arginine selective aptamer") GACGA-GAAGGAGCGCUGGUUCUACUAGCAGGUAGGUCA-CUCGUC-3' (SEQ ID NO:3); Biosearch Technologies) were added by pipetting small volumes (1-2 µL) of high concentration stocks (~100 µM in $dH_2O$) into the aqueous phase to achieve a final [Aptamer]~2.5 µM. Subsequent addition of the appropriate ligand (adenosine, GMP, cytidine, thymidine, L-arginine, L-citruline; Sigma-Aldrich) was also performed by pipetting small volumes (1-2 µL) of high concentration stocks (~11-17 mM in $dH_2O$) into the aqueous phase. The LC orientation and textures were observed between crossed polarizers with an Olympus microscope (model BH2-UMA) modified for transmission mode.

The relative end-to-end distance of dual-labeled adenosine selective aptamer (FAM-5'-ACCTGGGGGAGTATT-GCGGAGGAAGGT-3'-TAMRA (SEQ ID NO:4), Biosearch Technologies) was measured using Förster Resonance Energy Transfer (FRET) spectroscopy. The dual-labeled aptamer (100 nM) was constituted in buffer at varying ionic strength ([$Na_2PO_4H$]-7.8-100 mM) in the absence and presence (2 mM) of adenosine. Using a fluorescence plate reader (Wallac 1420 VICTOR, Perkin Elmer) we excited the dual-labeled aptamer at $\lambda_{ex}$=485 nm and measured the emission intensity at $\lambda_{d,em}$=528 nm ($F_D$, donor emission intensity) and $\lambda_{a,em}$=585 nm ($F_A$, acceptor emission intensity). These intensities were used to determine the relative distance between fluorophores according to equation 1: $d=(F_D/F_A)^{1/6}$ (Eq. 1). This equation was simplified from an equation that defines the absolute distance between fluorophores. This relative comparison of the distance between fluorophores was sufficient to make inferences about the nucleic acid conformations. Since the FRET pair is tethered on opposing ends of the DNA strand this relative separation between fluorophores is directly proportional to the relative end-to-end distance of the DNA.

Circular dichroism (CD) spectroscopy (Chirascan™-plus CD Spectrometer, Applied Photophysics) was used to probe the conformational changes that occur with varying ionic strength and upon addition of ligands. Each of the aptamer was constituted in 2.5 mM or 100 mM aqueous $Na_2PO_4H$ at 10 µM to a total volume of 300 µL. After measuring the CD spectra in the absence of ligand, 30 µL of a concentrated ligand stock ([Adenosine]≈600 µM, [Arginine]≈6600 µM) was added directly to the sample cuvette and mixed via pipetting to achieve a [ligand]≈10*$K_d$ for both aptamers. The CD spectra of pure buffer were also measured at [$Na_2PO_4H$]≈2.5 mM and 100 mM, as well as adenosine and arginine in the absence of aptamer under both these buffer conditions. The data obtained was reported in terms of ellipcity ($\theta$). After subtracting the buffer baseline, ellipcity, $\theta$, was converted to molar circular dichroism ($\Delta\epsilon$) according to equation S4: $\Delta\epsilon=[(\theta/32.983)/C \times l$ (Eq. S4), where C is the concentration of nucleic acid in moles of nucleobases and l is the optical path-length. Finally, the ligand contribution to $\Delta\epsilon$ was subtracted on a per mole basis and applied the Savitzy-Golay algorithm to smooth the resulting CD spectra.

Image Analysis:

Polarized light microscopy images were analyzed using ImageJ (NIH Freeware) to determine the fractional increase in fractional homeotropic ($f_H$) (or planar [$f_P$]) area upon addition of target. The images were first binarized using a common threshold value that allowed for a qualitative distinction between birefringent (bright) and homeotropic (dark) regions. It is noted that this binarization did not provide a pure measure of the fractional homeotropic area, since azimuthal orientation of the LC around defects resulted in extinction. However, normalizing the fraction of dark pixels within a pore of the grid by the average fraction of dark pixels at $c_o$ and at saturation accounted for the dark pixels that were not due to homeotropic LC orientation. This normalization was confirmed through qualitative inspection to verify that at $c_o$ there were no homeotropic domains and at saturation the grids were in fact 100% homeotropic. Equation S1 was used to calculate the fractional homeotropic area at a given concentration (c), where $f_x$=fraction of dark pixels at c, $f_o$=fraction of dark pixels at $c_o$, and $f_f$=fraction of dark pixels at saturation. To calculate $f_p$, all dark pixel fractions were replaced with bright pixel fractions in equation S1:

$$f_H = (f_x - f_o)/(f_f - f_o) \tag{Eq. S1}$$

Figure 5:
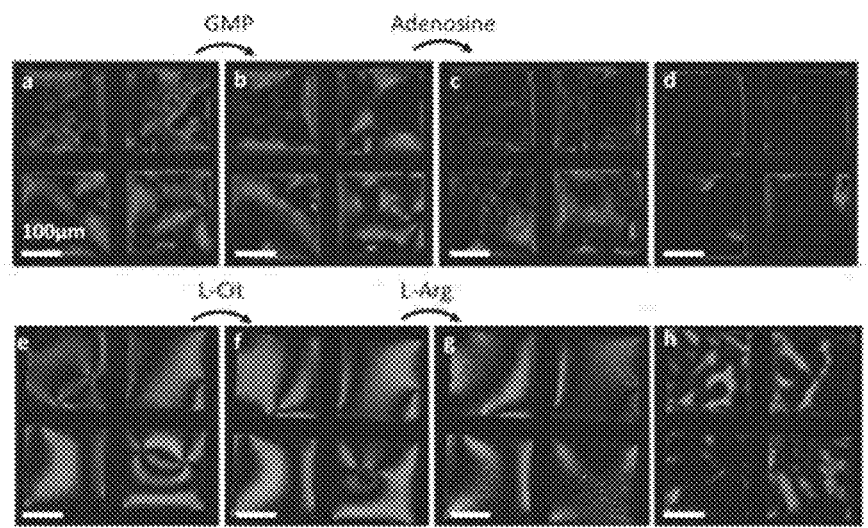
FIG. 5 shows polarized light microscopy images before and after addition of ligands. In particular, Panels a and e are images of the aqueous/LC interface laden with OTAB after adsorption of adenosine and arginine aptamers, respectively. Panels b and f are images about 3 min after addition of either GMP (300 µM) or L-cit (1 mM), respectively. Panels c and g are images about 30 sec after addition of either adenosine (300 µM) or Arginine (1 mM), respectively. Panels g and h are images about 5 min after addition of either adenosine or arginine, respectively.
Figure 6:
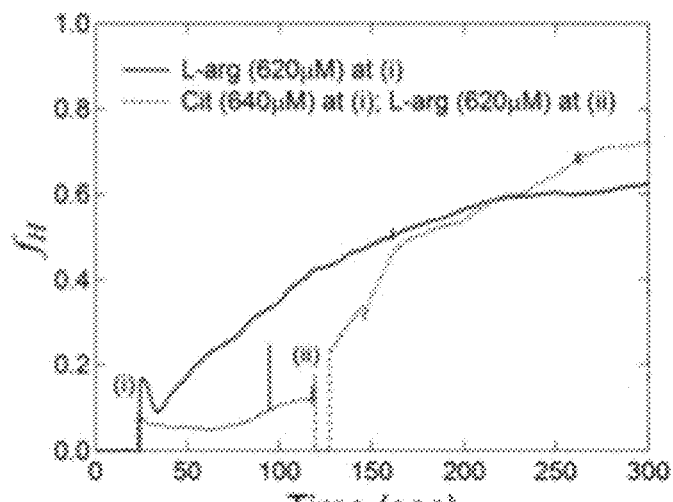
FIG. 6 shows graph of dynamic LC response upon addition of ligands arginine.

LC Response Specificity:

The specificity of the LC response was tested qualitatively through visual inspection of polarized light microscopy images and quantitatively via measuring the time dependence of $f_H$. The LC reorientation for the adenosine and arginine aptamer were found to be specific to their appropriate target. FIG. 5 shows images that supplement the plots displaying the time dependence of $f_H$ (FIG. 1, panel c, FIG. 6). While a specific response for both aptamers under the appropriate conditions were consistently achieved, the specificity of the adenosine aptamer was mildly sensitive to pH. At pH<7, a slight response to GMP was observed. However, this response observed to GMP was consistently less than that to adenosine. For example, in a sample that allowed for a transition to 100% homeotropic coverage upon addition of adenosine, the LC reorientation upon addition of GMP (at low pH) caused nucleation of homeotropic domains but the steady state homeotropic coverage was only ~20-40% of that observed for adenosine. This indicated a finite dissociation constant between GMP and the aptamer at pH<7 while at pH>7 the dissociation constant was so large that no significant LC reorientation was observed (due to minimal association of GMP-aptamer complexes). The dissociation constant likely varied with pH since guanosine is deprotonated at high pH (pKa≈9)[1]. This deprotonation may have induced an electrostatic repulsion between the negatively charged DNA and guanosine. In contrast, adenosine was not deprotonated at high pH and remained neutral, explaining the specificity of aptamer binding at pH>7.

CD Spectroscopy Analysis:

CD spectroscopy reports how circularly polarized light interacts with chiral molecules. As such, conformational inferences of polymeric molecules can be made by comparing experimental CD spectra to the spectra of well-known structures. CD has been extensively used for measuring conformations of proteins and nucleic acids and models have been developed correlating the observed CD spectra with a well-defined structure. While these models for calculating the CD spectra of nucleic acids have been successful in some cases, a comprehensive strategy for extrapolating high resolution structures from CD spectra of nucleic acids has yet to be realized, especially when studying aptamer-ligand complexes. It is well known that base stacking, and consequently DNA sequence, is one of the major contributors to the CD spectra of nucleic acids. While this area has been well studied, the contribution of non-Watson-Crick base pairing or interactions with ligands is not as well studied, making it difficult to apply a model for structures that involve these types of interactions (i.e., aptamer-ligand complexes). For these reasons, the structural inferences made here involve comparing the spectra of known nucleic acid conformations to observed experimental data.

From the CD spectra of the free adenosine and arginine aptamer at high and low ionic strength it was shown that the adenosine aptamer was in a random coil at low ionic strength and a weak hairpin at high ionic strength, while the arginine aptamer was in a random coil at low and high ionic strength. The CD spectra of the free adenosine aptamer upon increasing the ionic strength revealed the appearance of a shoulder at ≈210 nm, a decrease in the negative peak at and an increase and shift of the positive peak at ≈270 nm. While the exact spectral shifts are dependent on sequence, the appearance of a shoulder at ≈210 nm and the shift of the peak at ≈270 nm upon ligand binding were consistent with previous studies of the CD spectral changes that occur during DNA melting. Thus, it was concluded that the adenosine aptamer forms a weak hairpin at this increased ionic strength. The CD spectra of the free arginine aptamer at high and low ionic strength revealed no significant spectral differences. At low ionic strength (2.5 mM [$Na_2PO_4H$]) minimal electrostatic screening was expected and consequently a random coil configuration. As the ionic strength was increased to 100 mM, it was unclear what configuration to expect since there was a potential for significant electrostatic screening, but since no significant spectral shifts was observed at this ionic strength it was concluded that the ssRNA remained in a random coil configuration even at increased ionic strength. Furthermore, the observed spectra is consistent with others previously reported for ssRNA.

Figure 7:
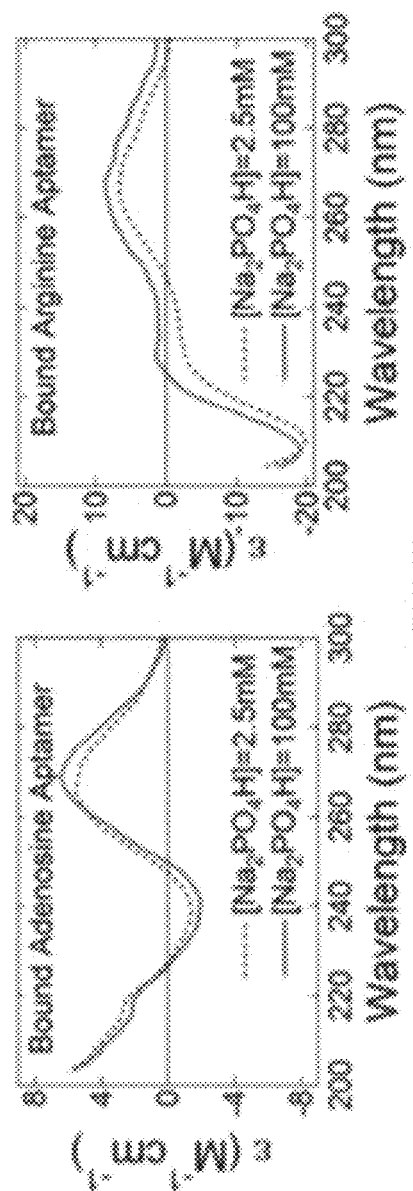
FIG. 7 is CD spectra of aptamers bound to their appropriate target at varying ionic strength.

The CD spectra of these aptamers in the presence of ligand at ≈10$K_D$ (FIG. 7) were also measured. For both aptamers dramatic shifts in the CD spectra at high and low ionic strength was observed, which is consistent with reported crystal structures. Upon binding, the adenosine aptamer is known to undergo Watson-Crick base-pairing at its tails and form a G-quadraplex structure at its head. These types of conformational changes are known to induce large CD spectral shifts. However, the CD spectrum expected from the aptamer-ligand complex is expected to be an average of the contributions from the double helix structure and the G-quadraplex structure, thus a theoretical spectrum of this structure would provide little value over an empirical comparison. The observed spectral shifts upon addition of adenosine, at low and high ionic strength, involved an increase and shift to lower wavelength in the positive peak at ≈270 nm, a decrease in the negative peak at ≈260 nm, and an increased CD signal at λ<210 nm. Previous CD spectral studies of DNA melting are consistent with the spectral shifts of the peak at as mentioned above. The literature on the CD spectra of the G-quadraplex known to form for the adenosine aptamer (antiparallel) are consistent with the present observation of a decrease in the negative peak at ≈240 nm and an increase in the positive peak at ≈270 nm. It is also noted that the CD spectral shifts that occur upon G-quadraplex formation are more dramatic than those that occur upon helix formation, explaining why a dramatic change in the CD spectra at ionic strengths (≈100 mM [$Na_2PO_4H$]) was seen where the ligand binding is not expected to induce significant Watson-Crick base pairing. The arginine aptamer revealed a decrease in the negative peak at ≈205 nm upon ligand binding. This shift occurred at high and low ionic strength, consistent with ligand binding under these conditions. CD studies of RNA have revealed that an increased intensity of the negative CD peak at ≈205 nm is consistent with Watson-Crick base pairing. The spectral shifts of the base pairing are highly dependent on sequence and usually also involve an increase in the CD peak at ≈265 nm. However, the structural changes that are known to occur do not purely involve base pairing but rather involve hydrogen bonding of the bases in the binding pocket with arginine as well as base pairing in other parts of the RNA strand. Nevertheless, the increased intensity of the negative CD peak at 205 nm is consistent with calculations and observations from the literature and is a good indication of ligand binding to the arginine aptamer.

Discussion:

LC-based sensing schemes have proven capable of specific signal transduction through LC reorientations driven by interfacial enzymatic reactions or molecular binding events. The unique interfacial phenomena that lead to LC reorientation in these systems are complex and subtle, often involving the competition between multiple non-covalent intermolecular interactions. The intrinsic cooperative behavior associated with the long-range orientational order of the LC phase provides a natural amplification effect, eliminating the need for (bio)chemical amplification, labeling, and/or expensive instrumentation. Some aspects of the present invention is based on the present inventors' belief that LC-based detection of aptamer binding would provide a potential path forward for label-free multiplexed un-amplified detection of multiple target types (e.g., small molecules, nucleic acids, proteins (including antibodies), etc.). The simultaneous detection of multiple molecular species in a label-free sensor scheme is an important goal, with widespread applications in areas including environmental monitoring, bio/chemical warfare detection, medical diagnostics, as well as other areas where a diagnostic system is used. It should be noted that one skilled in the art can readily recognize other diagnostic applications having read the present disclosure and applying the underlying principles.

Without being bound by any theory, it is believed that binding events associated with a nucleic acid conformational change at the aqueous/LC interface can be used as a detection mechanism. Specifically, aptamers that are known to bind to the small molecule targets adenosine and arginine were utilized to demonstrate the present invention. It should be appreciated that these aptamers were chosen as representative examples because they represent a DNA (adenosine) and RNA (arginine) aptamer and their target molecules possess significantly different structures.

Under the appropriate aqueous and interfacial conditions the present inventors have demonstrated the capability for aptamer-ligand binding events to induce a LC reorientation. When a sufficiently high surface concentration of cationic octadecyltrimethylammoniumbromide (OTAB) surfactant was adsorbed at an aqueous/LC interface, the LC orientation was homeotropic as expected (see FIG. 1, panel b(i)). Upon adsorption of aptamer (either the adenosine- or arginine-selective aptamer) to the OTAB laden aqueous/LC interface, a transition to tilted/planar LC orientation (FIG. 1, panel b(ii)) occurred. This reorientation indicates that, under these aqueous conditions, the interfacial structures of both aptamers exhibited substantial ssDNA character (i.e., with exposed hydrophobic nucleobases). When the appropriate target was subsequently added, the reverse LC reorientation occurred, characterized by the nucleation and growth of small homeotropic domains (FIG. 1, panel b(iii)) that eventually coalesced to give a consistent homeotropic orientation (FIG. 1, panel b(iv)).

Figure 4:
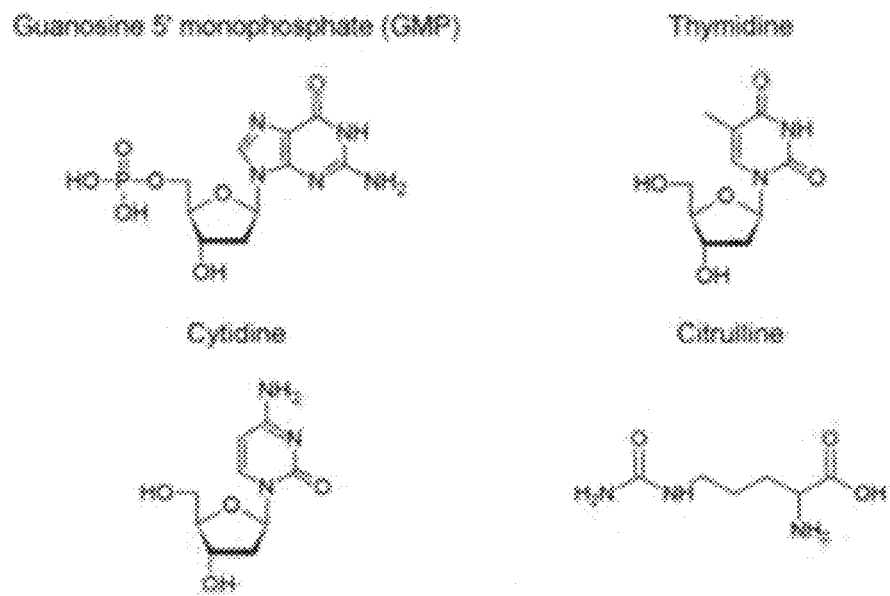
FIG. 4 shows chemical structure of control species

Several control experiments were performed in order to demonstrate the specificity of the LC response to aptamer binding. The LC response upon addition of cytidine, thymidine, and guanosine 5' monophosphate (GMP) to an adenosine aptamer laden interface, and upon addition of citrulline to an arginine aptamer laden interface, was tested. (FIG. 4) Furthermore, the LC response upon addition of adenosine to an interface laden with an adenosine aptamer containing a single base mismatch was also tested. In all of these control experiments, no LC reorientation was observed (e.g., FIG. 5) under the appropriate aqueous conditions (2.5 mM $Na_2PO_4H$, pH=7.3, supplementary information). To further illustrate this point, the time-dependence of the increase in fractional homeotropic area ($f_H$) extracted from polarized light microscopy images were measured, providing a quantitative signature of the LC reorientation (FIG. 1, panel c, FIG. 6). In these experiments, the addition of the appropriate aptamer consistently induced a transition to tilted/planar orientation. When adenosine or arginine was added ~30 sec after stabilization of the planar LC orientation ($t_i$) a distinctive increase in homeotropic coverage was observed over the following several minutes (solid black curves in FIG. 1, panel c and FIG. 6). If GMP or citrulline was instead added at $t_i$, no increase in the homeotropic coverage was observed (dotted red curves in FIG. 1 panel c and FIG. 6) until adenosine or arginine was subsequently added. These experiments demonstrated specificity consistent with the requirements for multiplexed detection, as a target-specific LC reorientation occurred in the presence of interfering ligands with very similar structures to the target.

The sensitivity and quantitative nature of the LC response was tested by "dose-response" experiments (FIG. 1, panel d). Small amounts of adenosine or arginine were added to the aqueous phase after adsorption of the appropriate aptamer at an OTAB laden aqueous/LC interface; polarized light microscopy images were obtained upon stabilization of the LC orientation. A LC reorientation, characteristic of the specific response described above, was observed at bulk concentrations consistent with previously reported disassociation constants for aptamer-ligand binding (dashed lines in FIG. 1, panel d). This systematic increase in homeotropic coverage observed with increasing concentrations of ligand provided a direct correlation between the LC reorientation and aptamer-ligand complex formation.

Figure 2:
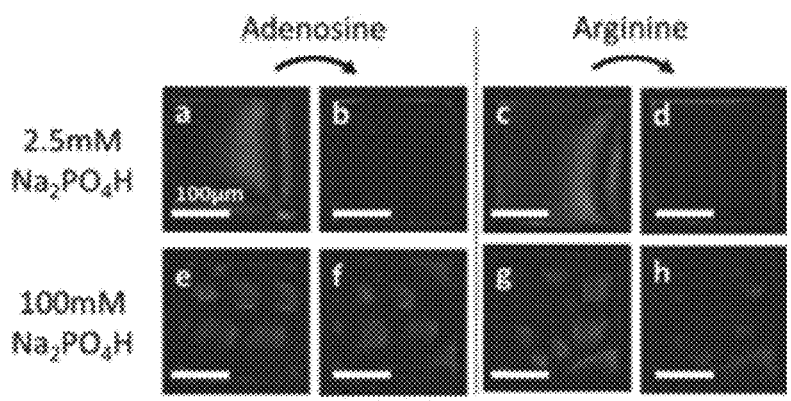
FIG. 2 shows polarized light microscopy images of the OTAB-laden aqueous/LC interface at varying ionic strength (panels a, c, e, and g) and after aptamer addition (panels b, d, f and h) about 3 min after subsequent addition of the appropriate ligand.

The operating conditions used in the experiments described above involved a relatively low ionic strength ($[Na_2PO_4H]$≈2.5 mM). Under these conditions a significant increase in the planar LC area upon adsorption of either aptamer (FIG. 2, panels a and c; Table 1) and a subsequent increase in the homeotropic area upon aptamer-ligand binding (FIG. 2, panels b and d; Table 1) were consistently observed. However, at higher ionic strength ($[Na_2PO_4H]$ 100 mM) it was expected that changes in the interfacial environment and the bulk nucleic acid conformation would affect the ability to achieve LC orientational transitions. Increased ionic strength in the bulk aqueous phase screens electrostatic interactions between the cationic head groups of the surfactant adsorbed at the aqueous/LC interface, allowing them to pack more tightly. Perhaps more importantly, similar electrostatic screening of the anionic DNA backbone at high ionic strength promotes DNA folding into a tightly wound random coil or, if the sequence permits it, a hairpin like structure. Both of these phenomena inhibit the ability for the nucleobases of unbound aptamers to interact with the LC subphase and perturb the OTAB surface coverage. Consequently, a decreased LC response to unbound aptamer adsorption under conditions of higher ionic strength was expected. It was observed that, for the adenosine and arginine aptamers, the fractional increase in planar area, $f_P$, indeed decreased at higher ionic strength (FIG. 2, panels e and g; Table 1).

TABLE 1

| Aptamer | (Na$_2$PO$_4$H) | f$_P$ | f$_H$ |
|---|---|---|---|
| Adenosine | 2.5 mM | 0.91 ± 0.10 | 0.88 ± 0.38 |
| | 100 mM | 0.37 ± 0.10 | 0.15 ± 0.07 |
| Arginine | 2.5 mM | 0.47 ± 0.09 | 0.66 ± 0.10 |
| | 100 mM | 0.14 ± 0.14 | 0.50 ± 0.39 | f$_P$: fractional increase in planar area upon addition of aptamer;
f$_H$: fractional increase in homeotropic area upon addition of appropriate ligand.

It was also believed that the subsequent LC reorientation upon aptamer-ligand binding relied on a significant decrease in the hydrophobicity of the adsorbed nucleic acid. However, a conformational change from a tightly wound random coil or hairpin structure may not involve a sufficiently dramatic change in nucleobase exposure to perturb the competitive balance for adsorption sites between DNA and OTAB. In fact, it was observed that, at high ionic strength, ligand binding to the adenosine aptamer failed to induce a significant LC reorientation (FIG. 2, panels e-f) while ligand binding to the arginine aptamer revealed a qualitatively similar response to that observed at lower ionic strength (FIG. 2, panels g-h; Table 1). This indicated that, at [Na$_2$PO$_4$H]≈100 mM, the conformational change of the adenosine aptamer upon ligand binding involved an insignificant change in nucleobase exposure, as it would expect if the free adenosine aptamer was already in a folded (i.e., hairpin) conformation prior to ligand binding. Conversely, ligand binding to the arginine aptamer still involved significant changes in nucleobase exposure at high ionic strengths, indicating the free arginine aptamer was in a coil conformation at the increased ionic strength tested. Structural studies, described below, are consistent with this model.

Förster resonance energy transfer (FRET) measurements of a dual-labeled adenosine aptamer and circular dichroism (CD) spectroscopy provided the basis for these structural studies. With increasing ionic strength, the relative end-to-end distance d (calculated from FRET measurements) decreased for both free and bound aptamer due to increased electrostatic screening (FIG. 3, panel a), as expected; however, this decrease was much more dramatic for the aptamer in the absence of ligand. Based on the model described above, a large difference in the end to end distance ($\Delta d_{low}$) between the free and bound aptamer at low ionic strength (i.e., dramatic conformational change) was expected and a significantly smaller difference ($\Delta d_{high}$) at high ionic strength (i.e., subtle conformational change) was expected. Consistent with these expectations, it was found experimentally that $\Delta d_{low} \gg \Delta d_{high}$.

Short end-to-end distances of nucleic acids are indicative of either a tightly packed globular coil state or a hairpin-like structure. While FRET measurements cannot distinguish between these two states, inferences can be made based on the known conformations of the adenosine-aptamer ligand complex. Past studies have shown that the adenosine aptamer forms a highly folded aptamer-ligand complex where the 5' and 3' tails of the DNA are adjacent, analogous to a hairpin conformation. Under an assumption that the aptamer-ligand complex at low ionic strength was in such a configuration, it was conclude that the free aptamer at high ionic strength was also in a hairpin conformation, since d for this free aptamer was within 3% of that for the bound aptamer at low ionic strength.

CD spectroscopy measurements further elucidated the aptamer conformations. The formation of hairpin like structures in nucleic acids result in characteristic CD spectral shifts while a transition from a loose random coil to a more compact globular structure is not expected to induce significant spectral shifts (supplementary information). The CD spectra of the free adenosine aptamer revealed spectral shifts at increased ionic strength (FIG. 3, panel b), consistent with hairpin formation, providing further evidence that the inability for ligand binding to induce a LC reorientation at increased ionic strength was related to an insignificant change in nucleobase exposure. Furthermore, the CD spectra of the free arginine aptamer was unvarying at high and low ionic strength (FIG. 3, panel c), indicative of a coil structure in both cases. This was consistent with a significant change in nucleobase exposure upon ligand binding (and the associated LC reorientation) at all ionic strengths measured. The CD spectra following addition of the appropriate ligand was also measured (FIG. 7) at concentrations ≈10K$_d$, and observed spectral shifts indicative of conformational changes, providing evidence that ligand binding occurred for both aptamers at both ionic strengths tested.

Figure 3:
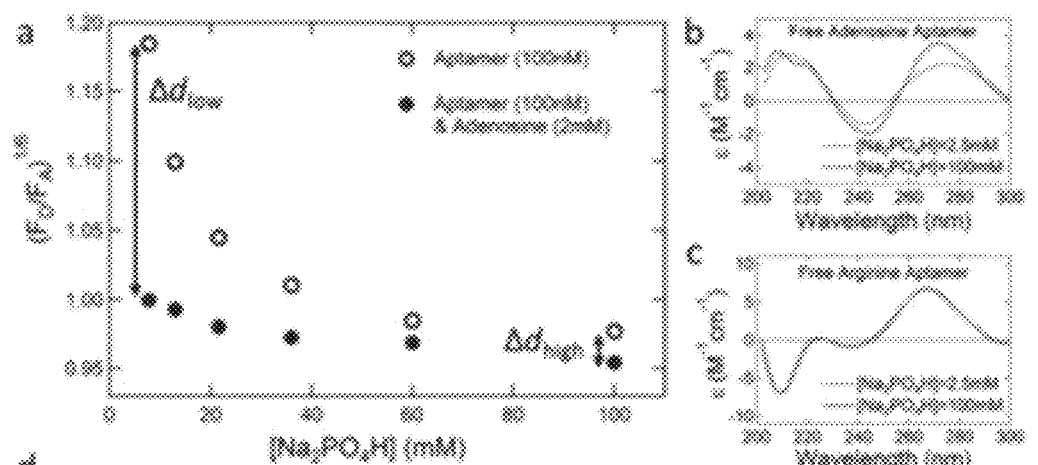
FIG. 3 shows aptamer structural studies data and schematic illustration of aptamer-ligand binding. In particular, panel (a) shows Forster resonance energy transfer of a dual-labeled adenosine aptamer at 25° C.; paned (b) shows circular dichroism (CD) spectra of 10 free adenosine aptamer; panel (c) shows CD spectra of 10 µM free arginine aptamer; and panels (d and e) show schematic of the proposed mechanism for aptamer adsorption and binding at an OTAB laden aqueous/LC interface.
Figure 3:
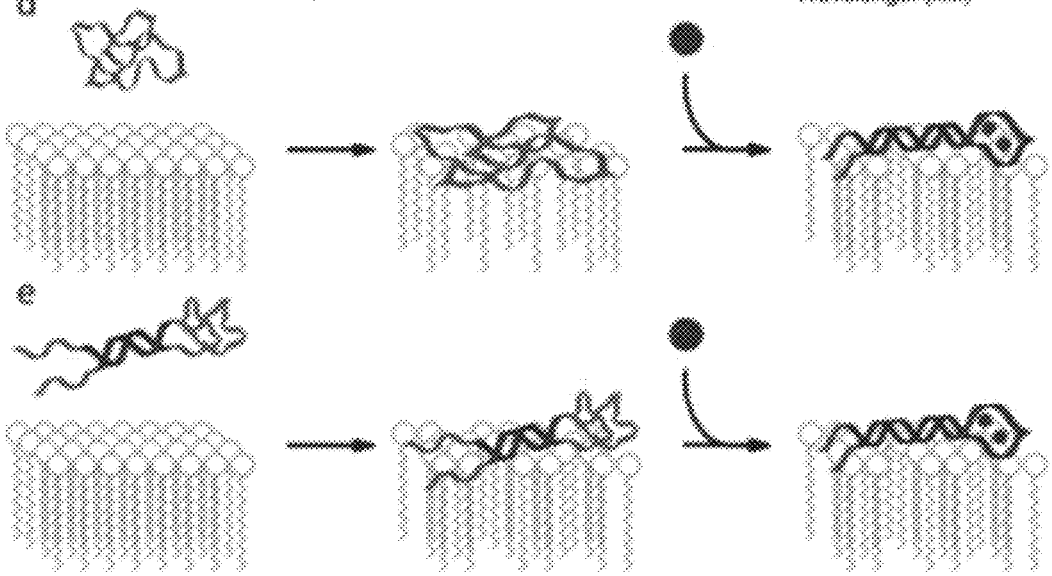

A mechanistic summary is schematically presented in FIG. 3, panels d and e. When the free aptamer is in a random coil conformation (FIG. 3, panel d, as for the adenosine aptamer at low ionic strength or the arginine aptamer at both low and high ionic strength), with exposed nucleobases, adsorption to the surfactant laden aqueous/LC interface results in an association between the exposed nucleobases and the LC subphase, via hydrophobic interactions, inducing a transition to planar/tilted LC orientation. Subsequent addition of the appropriate ligand results in a dramatic reduction in nucleobase exposure due to the formation of a highly folded aptamer-ligand complex, inducing the previously described transition to homeotropic orientation. Conversely, when the free aptamer is already in a folded conformation (e.g., a hairpin structure, FIG. 3, panel e), with few exposed nucleobases (the adenosine aptamer at high ionic strength), adsorption to the surfactant laden aqueous/LC interface fails to cause a strong transition to planar LC orientation. Subsequent addition of the appropriate ligand may induce the formation of some intricate tertiary structures (e.g., G-quadraplex), but since the aptamer transitions from a weakly folded hairpin to these tertiary structures there is little change in the amount of exposed hydrophobic bases. Consequently there is a negligible change in the competitive balance between the DNA and the interfacial OTAB for adsorption sites and the LC orientation is substantially unaffected by the addition of ligand in this case.

The discovery disclosed herein provides mechanistic principles that can be used in a wide variety of LC based aptasensing, i.e., detection of the presence of aptamer-ligand binding complex. The underlying mechanisms of LC anchoring are complex and potentially involve a range of non-covalent interactions including electrostatic, coordination, and steric effects. In the examples disclosed herein, it was find that a deviation from a homeotropic LC anchoring state, associated with the interdigitation of the calamitic LC between surface bound alkyl surfactants, occurred when an amphiphilic polymer (i.e., single stranded nucleic acid) effectively competed with these surfactants for adsorption sites. The examples also show a direct relationship between the amphiphilic nature (i.e., nucleobase exposure) of the adsorbed nucleic acid and the LC anchoring. The direct relationship between nucleic acid structure and the LC anchoring presented here shows how relatively subtle changes in amphiphilic adsorbates can induce LC reorientations. This broadly applicable and controllable conformational change in a surface bound species to induce a predictable LC anchoring transition can be used in a wide variety of highly multiplexed aptasensing applications.

This aptasensing scheme is label-free and utilizes LCs as a transduction element that responds to conformational changes in the aptamer upon ligand binding. Importantly, the non-specific adsorption of free aptamer did not induce a false-positive, but in fact promoted a negative response (planar LC orientation). It should be emphasized that the methods disclosed herein is significantly different from the previously disclosed aptasensing strategies that rely on efficient rinsing of non-specifically adsorbed species, a technique that is not applicable for highly-multiplexed applications. Moreover, multiplexed detection of aptamer targets disclosed herein can be readily combined with simultaneous detection of nucleic acid targets via hybridization. One skilled in the art having read the present disclosure can readily recognize that one can determine the appropriate interfacial conditions, such as surface charge density and surfactant composition, for the rational design of arrays for the simultaneous detection of a range of aptamer targets in a complex media (e.g., waste water, serum, etc.).

Example 2

The prominence of receptor-mediated bilayer fusion in cellular biology motivated development of biomimetic strategies for studying fusogenic mechanisms. This example is directed to an approach for monitoring receptor-mediated fusion that exploits the unique physical and optical properties of liquid crystals (LC). PEG functionalized lipids were used to create an interfacial environment capable of inhibiting spontaneous liposome fusion with an aqueous/LC interface. Then, oligonucleotide hybridization was exploited between oligonucleotides within bulk phase liposomes and a PEG-lipid monolayer at an aqueous/LC interface, to induce receptor-mediated liposome fusion. These hybridization events induced strain within the liposome bilayer, promoted lipid mixing with the LC interface, and consequently created an interfacial environment favoring re-orientation of the LC to a homeotropic (perpendicular) state. Furthermore, the bi-functionality of aptamers was exploited to modulate oligonucleotide hybridization mediated liposome fusion by regulating the availability of the appropriate ligand (e.g., thrombin). This example outlines a LC based approach for monitoring receptor (e.g., oligonucleotide hybridization) mediated liposome fusion, and shows how liposome properties dictate fusion dynamics, and provide an example of how this approach can be used in a bio-sensing scheme.

Understanding how to control bilayer fusion is fundamentally and technologically important for designing synthetic gene transfer agents, drug delivery strategies, studying biological systems, and developing diagnostic assays. In particular, in vivo biomimetic strategies for studying receptor-mediated fusion have played a major role in the advancement of this field. Since Rothman and coworkers first demonstrated that SNARE proteins were the minimum machinery required for inducing membrane fusion, they have been widely accepted as the most efficient fusogenic receptors. Their biological origin and prevalence in cellular membranes have inspired exploration of the mechanisms that allow SNARE proteins to work with such high efficacy. A common motif has been found among SNARE receptors that involve a bundle of four alpha-helices that associate upon recognition. The configuration of this quaternary structure induced strain to the associated lipid bilayers, initiating the fusogenic process. Several synthetic approaches that mimic this structural motif have been developed using peptides, model proteins, small molecules, and DNA in an effort to achieve efficient recognition, bilayer disruption, and content transport in vivo.

In particular, oligonucleotide hybridization-mediated fusion shows promise as a reductionist system both for studying fusion mechanics and as a bio-sensing strategy. Studies have shown that oligonucleotide can be anchored to lipid bilayers using oligonucleotide-lipid conjugates or sterol tethered oligonucleotide. Uni-lamellar liposomes can therefore be prepared with such tethered oligonucleotides. When two liposomes prepared with different but complementary oligonucleotides were combined, lipid mixing assays revealed bilayer fusion. One of the requirements in these assays was that membrane anchors on complementary oligonucleotide strands had to be on opposite ends of the oligonucleotide (i.e., 5' and 3' ends). In this configuration, oligonucleotide hybridization mimicked the configuration of the four helix bundle in SNARE receptors, brought the two bilayers into close proximity, strained the bilayer structure, and consequently induced efficient lipid mixing and content transport. In the alternative situation where the tethers are on the same end of the oligonucleotide, the liposomes were observed to aggregate but no observable lipid mixing or content transport occurred, presumably due to a lack of bilayer-bilayer proximity and strain.

Studying receptor-mediated fusion in dispersed liposomes is convenient for proof-of-concept studies but has limited capacity for advancing related technologies. Alternatively, receptor-mediated fusion with planar interfaces, and in particular supported lipid bilayers, has been used for quantitative high throughput studies that elucidate cellular mechanisms related to drug discovery, medical diagnostics, and biosensor development. Supported lipid bilayers can be fabricated as spatially addressed microarrays capable of high throughput screening and have demonstrated value as a tool for studying a range of biochemical processes. Despite their success as model systems, supported lipid bilayers possess complicating factors such as interfering effects associated with the underlying solid substrate and the necessity of complex and expensive analytical instrumentation. Thus, substrates that address some of these drawbacks have significant value toward a better understanding of liposome fusion from a fundamental and technological perspective.

The present inventors used an alternate system for monitoring liposome fusion with planar interfaces that employed a soft hydrophobic interface (e.g., liquid crystals) for depositing lipid monolayers with surface anchored receptors (e.g., oligonucleotide or DNA). It is believed that the hydrophobic nature of the LC substrate would minimally interfere with surface anchored components while also serving as a transduction element requiring only a simple optical set up for dynamic monitoring of fusogenic activity.

Liquid crystals (LCs) have become a valuable tool for monitoring interfacial phenomena at both solid and aqueous interfaces. Examples include self-assembly processes, the dynamic behavior of hydrophobic polyanions, protein binding and surfactant phase behavior. Studies have revealed that certain surfactants (e.g. those with long hydrocarbon tails) partitioned to the hydrophobic aqueous/LC interface, at sufficient surface densities, orient calamitic LC molecules with their long axes perpendicular to the surface (homeotropic orientation). Importantly, only surfactants with hydrocarbon chains longer than a certain threshold length were observed to induce homeotropic orientation. Among this class of surfactants were saturated phospholipids, which were deposited at the aqueous/LC interface via spontaneous liposome fusion. This spontaneous fusion was shown to be independent of lipid phase, and lipid/surfactant mixtures were employed to control the relative density of lipids within a monolayer at the aqueous/LC interface. Thus, spontaneous fusion of liposomes with LC interfaces has been well characterized and is readily monitored using the optical effects associated with LC re-orientation.

More recent studies have achieved specific control over interfacial LC orientational transitions by exploiting conformational changes in adsorbed biomolecules, localizing polar molecules via coordination interactions, or mediating surfactant deposition with biomolecules. In one example in particular, liposome fusion was controlled at protein decorated interfaces. Liposomes were prepared with biotinylated phospholipids and introduced to a streptavidin laden LC interface. Streptavidin inhibited spontaneous fusion of undecorated liposomes with the interface while also acting as a probe to detect biotin in dispersed liposomes. When biotin bound to streptavidin at the interface, liposome fusion was initiated, and a transition to homeotropic orientation was observed. This example provided a method for using specific binding events to deposit lipids at an aqueous/LC interface. A more general (and multiplexed) approach requires the incorporation of membrane-anchored receptors that are compatible with a generalizable interfacial environment for inhibiting spontaneous liposome fusion.

One of the goals of this example was to design a system for using biomolecular interactions to induce liposome fusion. To this end PEG-lipid laden aqueous LC interfaces, which are inherently resistant to non-specific adsorption, was utilized. It was believed that these interfaces would inhibit spontaneous liposome fusion and provide sufficient resistance to non-specific protein adsorption to enable the detection of specific protein binding events. Oligonucleotides were anchored to bilayers within liposomes and at the aqueous/LC interface and served as receptors for mediating liposome fusion. Using this experimental system, the present inventors set out to (i) observe and characterize oligonucleotide hybridization-mediated liposome fusion via a LC reorientation, (ii) explore the liposome properties that dictate the kinetics associated with these fusion events, and (iii) demonstrate the applicability of this approach in a detection scheme utilizing aptamers.

Materials:

Lipids (e.g., (1,2-distearoyl-sn-glycero-3-phosphoethanolamine-N-[methoxy(polyethylene glycol)-1000] (ammonium salt)) DSPE-PEG1k; (1,2-distearoyl-sn-glycero-3-phosphoethanolamine-N-[methoxy(polyethylene glycol)-2000] (ammonium salt)) DSPE-PEG2k; (1,2-distearoyl-sn-glycero-3-phosphoethanolamine-N-[methoxy(polyethylene glycol)-5000] (ammonium salt)) DSPE-PEG5k; 1,2-dipalmitoyl-sn-glycero-3-phosphocholine (DPPC)) were purchased from Avanti Polar Lipids Inc. Oligonucleotides (5'chol-oligonucleotide: CHOL—5'-TCCGTCGTGCCTT-ATTTCTGATGTCCAAAACCAACCACA-3' (SEQ ID NO:5); 3'chol-oligonucleotide: 5'-GTTGGTTTTGGA-CATCAGAAATAAGGCACGACGGA-3'-CHOL (SEQ ID NO:6), and aptamer: 5'-GGTTGGTGTGGTTGGTTT-3' (SEQ ID NO:7)) were purchased from IDT Technologies. Thrombin from human plasma (>1000 NIH units/mg) was purchased from Sigma-Aldrich and suspended in aqueous buffer at concentrations ranging from 3-10 μM as verified by absorption measurements at λ=280 nm (i.e. Nanodrop 2000). A liquid crystal mixture, E7 (a mixture of three cyano-biphenyls and a cyano-terphenyl), was purchased from Merck Kga. Aqueous buffers were prepared from powder stocks of Tris-HCl (Fisher) and NaCl (Fisher) constituted at the proper concentrations in deionized water (18.2 MΩ-cm) and adjusted to pH ~8.5 by addition of 0.1M NaOH. Octadecyltriethoxysilane was purchased from Gelest Inc. and deposited onto soda-lime glass microscope slides (Fisher) according to the procedure outlined below. Electron microscopy grids (CP-100) were purchased from Electron Microscopy Sciences. Silicone isolators were purchased from Grace Bio Labs and were used as wells to contain the aqueous phase above the LC interface.

Liposome Preparation:

Liposomes were prepared by first dissolving a known mass of the appropriate lipid in chloroform. Chloroform was then removed by rotary evaporation at ~55° C. with a rotation speed of 200-250 rpm to obtain a homogenous lipid film. The film was subsequently solvated in an aqueous buffer (10 mM Tris, 100 mM NaCl, pH ~8.5) at [lipid]~6.8 mM and incubated in a water bath at ~70° C. for 30-60 m. Once lipids were completely dispersed in aqueous buffer, the lipid solution was diluted to the desired concentration and added the applicable DNA strands at the appropriate concentrations. The lipid/oligonucleotide mixture was incubated at ~70° C. for 30-60 m to allow sufficient time to incorporate into the lipid bilayer. Finally, the vesicles were sized using a membrane extruder (Avanti Polar Lipids Inc.) with membrane pore sizes ($D_{pore}$) of 50, 100, or 400 nm. Liposome diameters were subsequently measured using photon correlation spectroscopy. DSPE-PEG micelles were always prepared at the same concentration by mixing DSPE-PEG (and 3'chol-oligonucleotide when applicable) with aqueous buffer (10 mM Tris, 100 mM NaCl, pH ~8.5) to a final [DSPE-PEG]≈40.2 μM ([3'chol-oligonucleotide]≈0.85 μM) and vortexing the mixture for 30-60 s.

LC Film Preparation:

Preparation of self-assembled monolayers (SAMs) of octadecyltriethoxysilane (OTES) was completed according to published procedures[25]. Briefly, glass slides were cleaned sequentially with 2% aqueous Micro-90 detergent, deionized water (18.2 MΩ-cm), and piranha solution (30% aqueous $H_2O_2$ (Fisher Scientific) and concentrated $H_2SO_4$ (Fisher Scientific) 1:3, v/v) at ≈80° C. for 1 h. Piranha-cleaned microscope slides were then rinsed with deionized water (18.2 MΩ-cm) and dried under a stream of ultrapure $N_2$. Toluene, OTES, and n-butylamine (Fisher Scientific) (Fisher Scientific) were mixed at 200:3:1 volumetric ratios, respectively, and warmed to 60° C. Clean and dry microscope slides were rinsed with toluene, submerged in the warm deposition solution, and incubated for 1 h at 60° C. Following this incubation, the slides were rinsed with toluene, dried under a stream of ultrapure $N_2$, and stored at room temperature in a vacuum desiccator. The water contact angle ($\theta_C$, measured via the static sessile drop method) of the prepared SAMs was verified to be >95° (indicative of strong homeotropic anchoring) using a custom-built contact angle goniometer.

Aqueous/LC interfaces were prepared by housing LC films within the pores of an electron microscopy grid. The grids were initially placed onto a solid glass substrate functionalized with an OTES self-assembled monolayer (SAM) and contained within silicone isolators. The SAM served to maintain homeotropic orientation of the LC at the solid substrate. The pores of the electron microscopy grid were then filled with E7 by pipetting ≈250 nL into the grid and removing the excess via capillary action. Next, the wells were filled with ~25 μL of an aqueous solution. When depositing DSPE-PEG micelles to the interface, aqueous buffer containing the appropriate DSPE-PEG micelles were added during this initial introduction of the aqueous phase. Liposomes were subsequently added two minutes after the initial introduction of the aqueous phase by pipetting an additional 25 µL of the desired liposome mixture, mixing the solution in the wells by pipetting, then removing 25 µL to re-establish the planar air-water interface that allows for efficient imaging (note: curvature of the air-water interface caused reflections that distorted polarized light microscopy images). The LC orientation and textures were dynamically monitored between crossed polarizers using a custom built transmission microscope.

Image Analysis:

Images obtained from polarized light microscopy (PLM) were analyzed using customized algorithms in the Mathematica programming environment. The region of interest was first selected using an image convolution function to find the center of the electron microscopy grid, and a constant grid diameter to select the region of interest for analysis. Next, images were binarized to obtain the fraction of dark pixels in a given image. However, this fraction of dark pixels did not directly correlate with homeotropic coverage since in-plane (i.e., azimuthal) alignment of LC molecules around point defects resulted in extinction at angles parallel or normal to the incident polarization of light. Since the surface area of LC film that experienced this extinction was relatively constant, this artifact was circumvented by using a normalization approach. The fractional increase in homeotropic coverage ($\Delta f_H$) was obtained as a function of time within a series of images according to the following equation:

$$\Delta f_H = (f_t - f_o)/(1 - f_o)$$

where $f_o$ was the fraction of dark pixels in a qualitatively planar image from the same time series and $f_t$ was the fraction of dark pixels at time=t.

Figure 14:
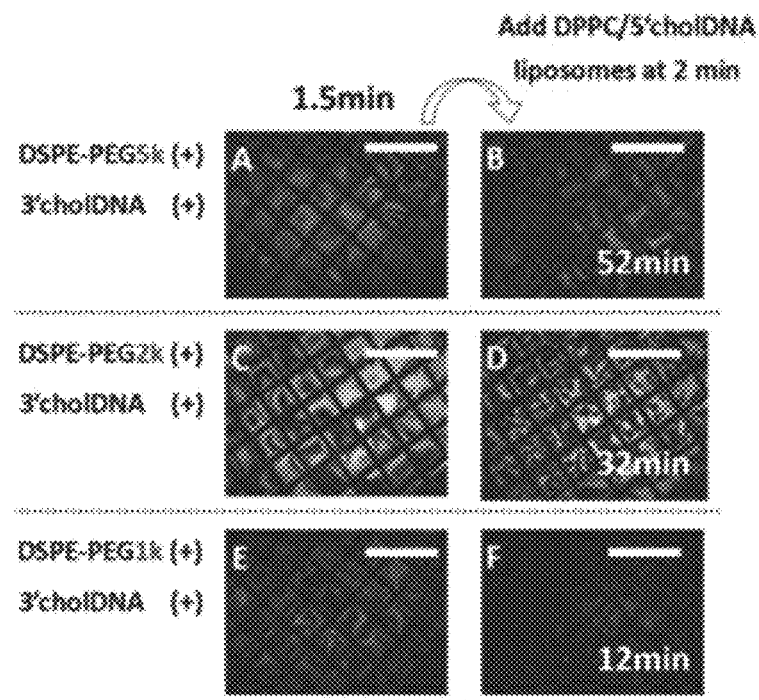
FIG. 14 shows polarized micrographs of the aqueous/LC interface after the initial addition (t=0 min) of DSPE-PEG/3'chol-oligonucleotide micelles with 5 kDa (Panels A and B), 2 kDa (Panels C and D), or 1 kDa (Panels E and F) PEG groups. Liposomes (DPPC/5'chol-oligonucleotide) were added at 2 minutes and the LC orientation after 52 minutes is shown when a 5 kDa PEG group was used (Panel B), 32 minutes when a 2 kDa PEG group was used (Panel D), and 12 minutes when a 1 kDa PEG group was used (Panel F). Scale bars are 500 µm.

Results and Discussion: Creating a Steric Barrier to Liposome Fusion:

While past studies have characterized the phase behavior of PEG-lipids at aqueous/LC interfaces, the extent to which these interfaces inhibit non-specific adsorption had not previously been determined. Thus, the first step involved characterizing DSPE-PEG (and 3'chol-oligonucleotide) laden aqueous/LC interfaces. When micelles comprised of PEG-functionalized DSPE (DSPE-PEG) and 3'chol-oligonucleotide were introduced to the aqueous phase in contact with the LC, no change was observed in the LC orientation from the native planar orientation observed at undecorated aqueous/LC interphases. This was true for PEG molecular weights ranging from 1-5 kDa (FIG. 14). Thus, under the assumption that the micelles fused with the bare LC interface, it can be concluded that the presence of a DSPE-PEG/3'chol-oligonucleotide monolayer was insufficient to cause a re-orientation of the LC phase. Another less likely hypothesis, however, was that the micelles did not fuse with the LC interface. As described below, the response of the interface to subsequent changes was used to test these hypotheses.

Figure 15:
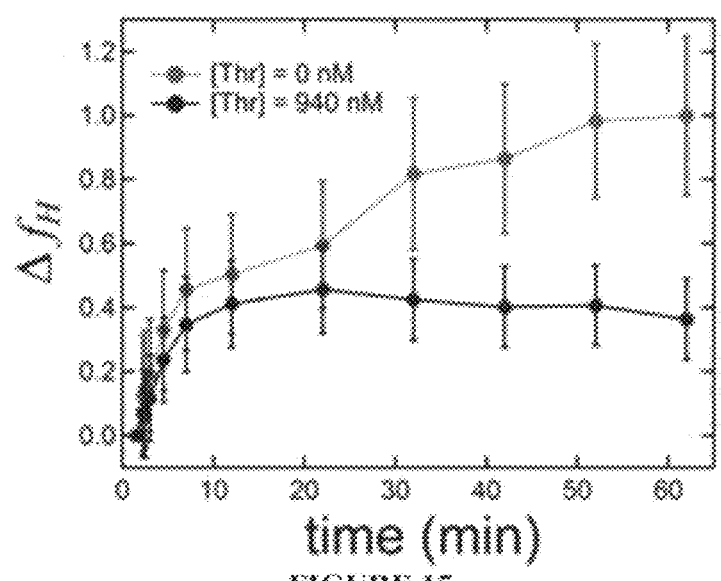
FIG. 15 is a data showing the fractional increase in homeotropic coverage plotted against time when DPPC liposomes were added to an undecorated LC interface at 0 min (both black and red curves) and thrombin was subsequently added at 2 min (black curve).

In particular, the ability of DPPC liposomes to fuse with the aqueous/LC interface was found to be sensitive to the presence (or absence) of a steric barrier (e.g., PEG). When DPPC liposomes were added to the aqueous phase in contact with an LC interface, a transition to homeotropic orientation occurred due to spontaneous fusion and deposition of lipids at the interface (FIG. 15). The driving force for this spontaneous fusion was believed to be the relative instability of these aggregate structures. DPPC, like most other saturated phospholipids, has a packing factor close to unity. These packing factors favor a planar lamellar configuration but form spherical bilayer aggregates in bulk solution to minimize the energy costs associated with open ends in planar lamellae. When a hydrophobic interface was accessible, the lipids partitioned to the interface and assembled into a favorable planar monolayer configuration without ends that were exposed to an aqueous environment.

Figure 8:
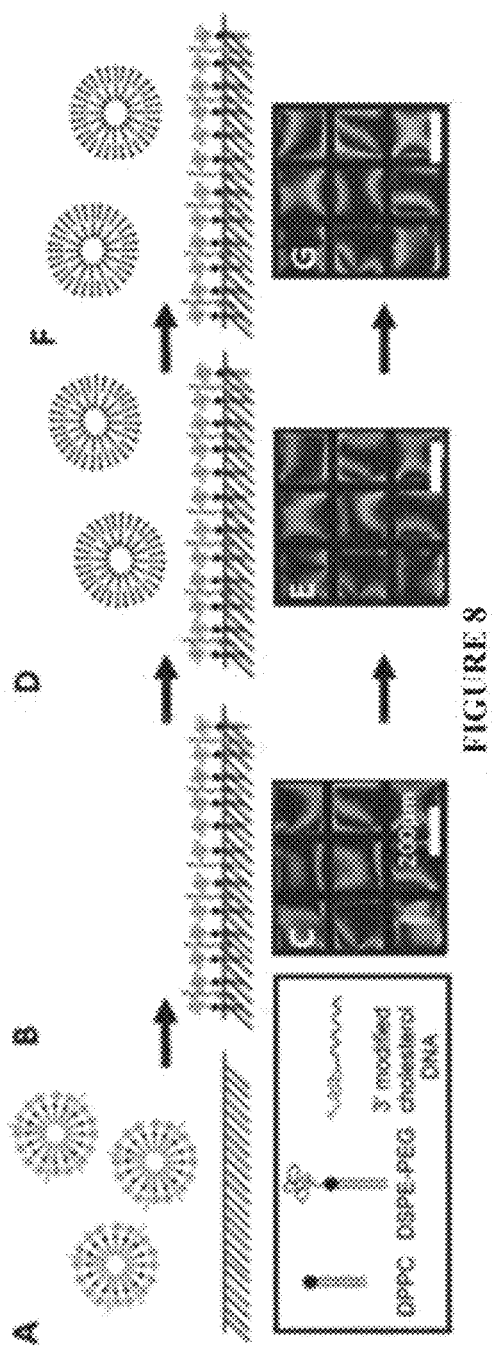
FIG. 8 shows schematic illustration and images of inhibiting spontaneous liposome fusion. In particular, panel (A) is illustration of adding DSPE-PEG1k/3'chol-DNA micelles to the aqueous phase in contact with a LC interface, panel (B) illustrates spontaneously fuse, panel (D) illustrates resulting in planar/tilted LC anchoring, and panel (F) illustrates when DPPC liposomes are subsequently added, no change in the LC orientation. Panel C is an image before addition of DPPC liposomes. Panel E shows no change in LC orientation after 1 m. Panel (G) shows no change in LC even after 60 m indicative of long-term fusion inhibition.

However, if there was a steric barrier at the interface, the proximity of the liposomes to the hydrophobic interface may be insufficient to induce spontaneous disruption of the bilayer structure. In fact, this was exactly what was observed, as illustrated in FIG. 8, where planar LC orientation was maintained for at least 1 h after adding DPPC liposomes to the aqueous phase in contact with a DSPE-PEG/3'chol-oligonucleotide laden interface. The same behavior was observed when 3'chol-oligonucleotide was not included in the micelles used to pre-load the interface, indicating that DSPE-PEG alone was sufficient to inhibit spontaneous liposome fusion. Importantly, this result verified that the DSPE-PEG micelles did in fact spontaneously fuse with the LC interface since their presence dramatically modified the interfacial fusion behavior of the DPPC liposomes. Thus, an interfacial environment capable of inhibiting spontaneous liposome fusion was successfully created.

Figure 9:
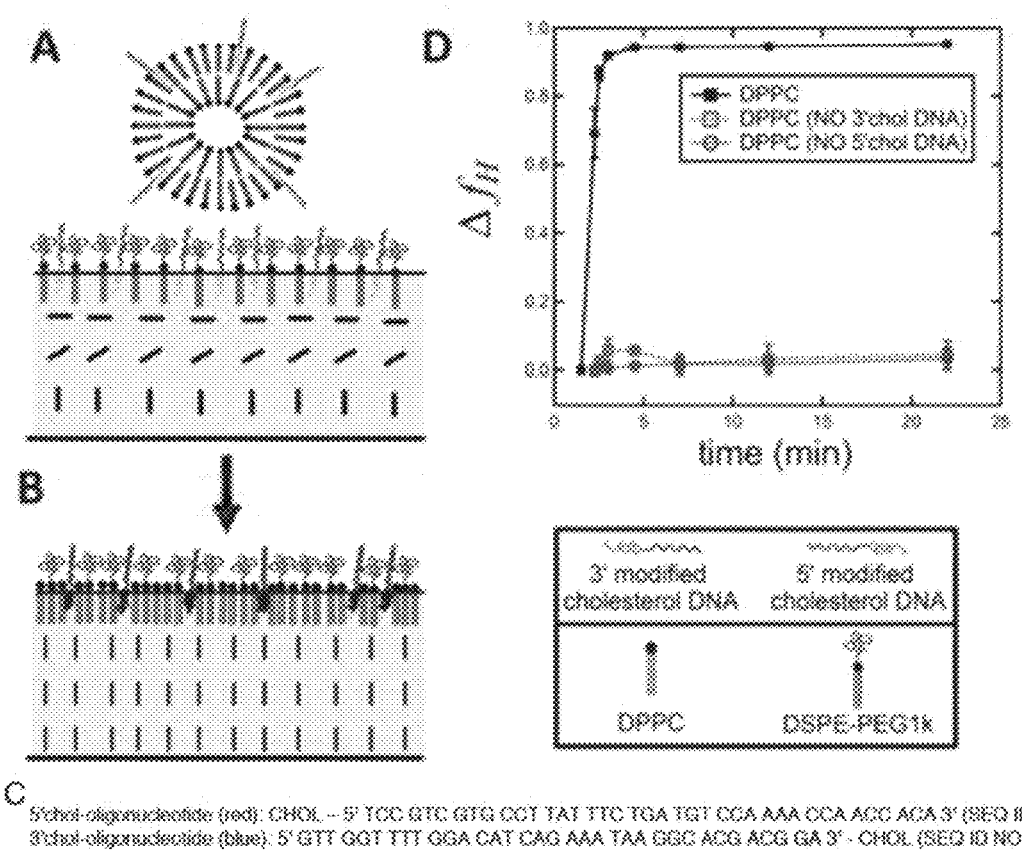
FIG. 9 shows schematic illustration and actual data for DNA hybridization mediated fusion. Panel A is a schematic representation of adding DPPC/5'chol-oligonucleotide liposomes above a DSPE-PEG1k/3'chol-DNA laden LC interface. Panel B is a schematic illustration showing oligonucleotide hybridization deposits DPPC at the interface to induce homeotropic LC orientation. Panel C shows oligonucleotide sequences used. Panel D shows the fractional increase in homeotropic area (AA) observed when adding liposomes ([DPPC]≈4.1 mM; [5'chol-oligonucleotide]≈1.6 µM; $D_{pore}$=50 nm) 2 minutes after the initial introduction of the aqueous phase. The black curve indicates that both 5'chol-oligonucleotide and 3'chol-oligonucleotide were present in their appropriate location while the red curve is the response when 3'chol-oligonucleotide was left out and the blue curve is the response when 5'chol-oligonucleotide was left out. Error bars represent the standard error associated with the experimental data.
Figure 10:
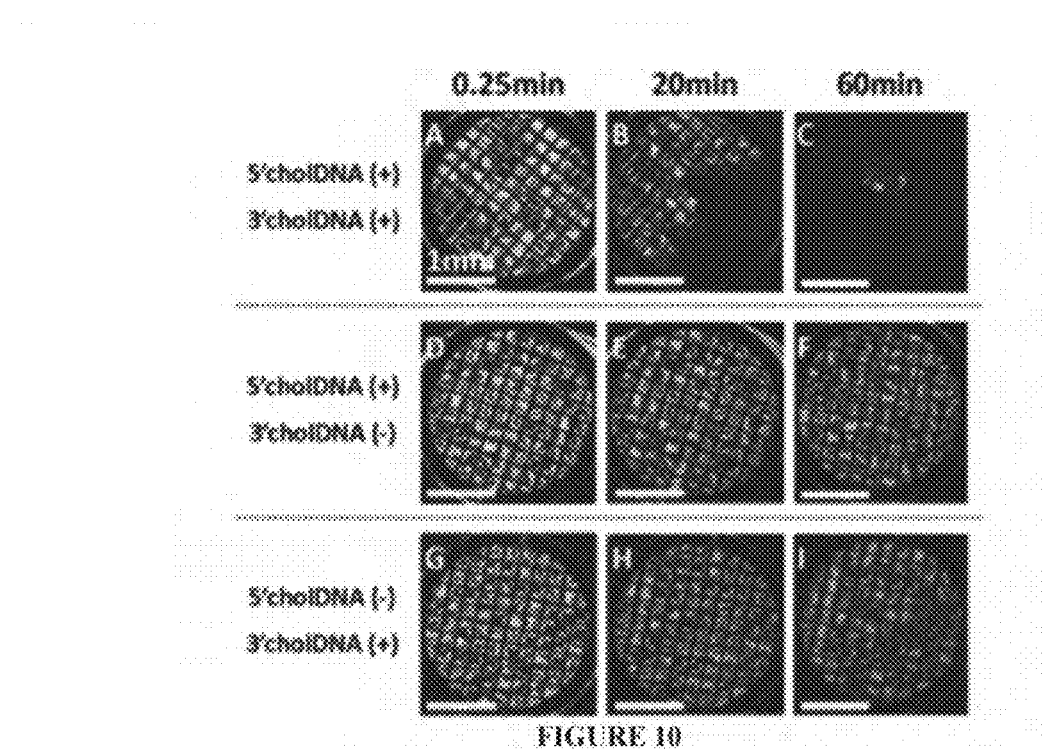
FIG. 10 shows polarized microscopy images of the aqueous/LC interface when either DPPC/5'chol-oligonucleotide (Panels A-C; D-F) or DPPC (Panels G-I) liposomes were added to either a DSPE-PEG1k/3'chol-oligonucleotide (Panels A-C; G-I) or DSPE-PEG1k (Panels D-F) laden interface. Images were taken at 0.25 min (Panels A, D and G), 1 min (Panels B, E and H), and 20 min (Panels C, F and I) after the introduction of liposomes. [DPPC]≈4.1 mM; [5'chol-oligonucleotide]≈1.6 µM; $D_{pore}$=50 nm.

Overcoming the Steric Barrier with DNA Hybridization:

Receptor binding (e.g., oligonucleotide hybridization) was utilized to overcome the steric barrier associated with liposome fusion to the PEG-laden LC interface. Receptor-mediated fusion involves two key steps: (1) recognition and (2) destabilization of the bilayer structure. It was believed that if 5'chol-oligonucleotide was anchored to liposomes and introduced to a LC interface laden with complementary 3'chol-oligonucleotide, then recognition (or docking) would occur between the liposomes and the interface. To further increase the likelihood of destabilization, a design where the complementary oligonucleotide strands had tethers that partitioned to the same interface after hybridization (FIG. 9, panels A-B) was used to induce strain in the liposome bilayer structure. Using this approach, receptor-mediated fusion between liposomes and the aqueous/LC interface was successfully demonstrated. Specifically, a transition to homeotropic anchoring was observed (FIG. 9, panel D and FIG. 10, panels A-C) upon addition of DPPC/5'chol-oligonucleotide liposomes to a DSPE-PEG1k/3'chol-oligonucleotide laden aqueous/LC interface. To verify that the lipid mixing was in fact receptor-mediated, control experiments was performed where the oligonucleotide was omitted from either the liposome or the planar interface. In both cases, it was found that no lipid mixing was observed (i.e., the LC orientation remained planar) (FIG. 9, panel D and FIG. 10, panels D-I). While previous studies have revealed that oligonucleotide hybridization alone can induce LC orientational transitions, the initial conditions in our system (i.e. surfactant and/or chol-oligonucleotide surface density) are insufficient for initiating these transitions. Thus, the observed transition to homeotropic orientation is likely due to oligonucleotide hybridization initiating the partitioning of DPPC to the interface.

Figure 16:
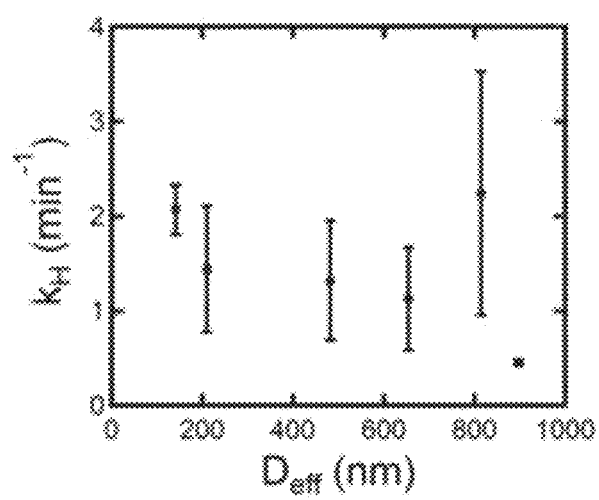
FIG. 16 is a graph showing an effective rate constant ($k_H$) representing the inverse of the time taken to reach 50% homeotropic coverage plotted against the effective liposomes diameter as determined by photon correlation spectroscopy. Error bars represent the standard error from the experimental data; [DPPC]≈4.1 mM; [5'chol-oligonucleotide]≈1.6 µM)

Consistent with the proposed mechanism, when the molecular weight of the PEG group tethered to DSPE-PEG at the interface was varied, a transition to homeotropic anchoring was observed only when the PEG molecular weight was <2 kDa (FIG. 14). Importantly, for each PEG MW tested, no liposome fusion was observed in the absence of 5'chol-oligonucleotide. These results suggested that when PEG groups were too large, the steric barrier was too great, consequently hindering either oligonucleotide hybridization or bilayer rupture. Also, when the liposome size was varied by extruding them through membranes with various pore sizes no significant change in the fusion kinetics was observed with liposome diameter (FIG. 16). This suggested that given the fast kinetics observed, an increase in the liposome mobility (smaller liposomes) or available lipids per liposome (larger liposomes) had an insignificant effect on the rate of lipid mixing.

Figure 11:
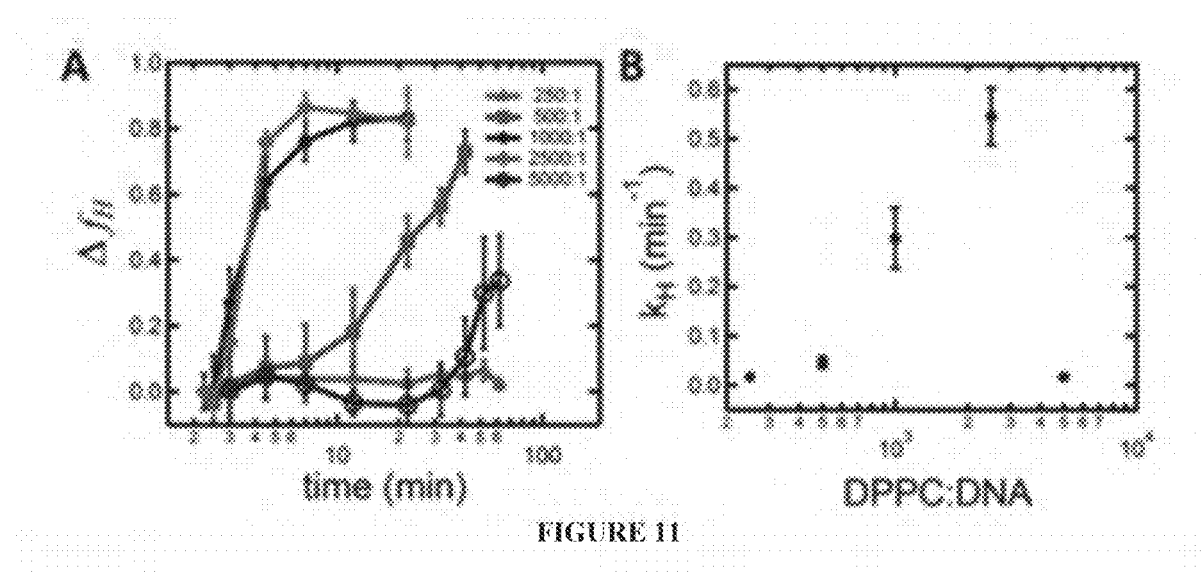
FIG. 11 shows date for 5'chol-oligonucleotide coverage. Panel A is a graph showing the fractional increase in homeotropic coverage observed at varying DPPC:5'chol-oligonucleotide ratios. Panel B shows the effective rate constant ($k_H$) which represents the inverse of the time required to reach 50% homeotropic coverage (upper limit=60 m) as interpolated from the data. [DPPC]≈4.1 mM; [5'chol-oligonucleotide]≈1.6 µM; $D_{pore}$=400 nm.

To better understand the effects of oligonucleotide coverage on receptor-mediated fusion kinetics the 5'chol-oligonucleotide content of the liposomes was systematically varied (see FIG. 11). Previous studies have shown that an increased coverage of oligonucleotide on unilamellar liposomes increased the kinetics of fusion between dispersed liposomes possessing complementary oligonucleotides. However, these studies addressed only a relatively narrow regime of DNA coverage and did not address the potential inhibition of fusion that could occur due to electrostatic repulsion between liposomes at high oligonucleotide coverage. As shown in FIG. 11, it was found that the rate of fusion was non-monotonic with respect to the DPPC:5'chol-oligonucleotide ratio. In the regime of high oligonucleotide content no indication of fusion (i.e., change in LC tilt angle) was observed on the time scales of the experiment, indicating complete inhibition of fusion. In this case, the electrostatic repulsion might have been so great that the probability of a hybridization event occurring was insufficient to induce liposome fusion. At low 5'chol-oligonucleotide coverage, a slower rate of lipid mixing was observed, but the fusion was not completely inhibited (FIG. 11, panel A). Here, it is believed that hybridization was still able to proceed but, because of the low surface density of oligonucleotide, the probability of oligonucleotide hybridization events occurring was significantly decreased. These experiments provided insight into how electrostatics and oligonucleotide density were dictating the fusion dynamics and provided with an optimal range to use for maximizing fusion kinetics.

Molecular Sensing Using Oligonucleotide Hybridization-Mediated Fusion:

Experiments were performed that demonstrated how this type of oligonucleotide hybridization mediated-fusion could be exploited for molecular sensing. In particular, aptamers were incorporated into the detection scheme to detect the presence of the protein thrombin. Aptamers are nucleic acids that are synthetically evolved using the SELEX (systematic evolution of ligands by exponential enrichment) process to bind to a specific target molecule (e.g., small molecules, antibodies, proteins). They have become attractive as probes for multiplexed based assays due to the high sensitivity and specificity with which they bind to their respective target. Since aptamers are nucleic acids, studies have shown that they possessed a degree of bi-functionality since they bound to complementary oligonucleotide strands, via hybridization, and appropriate molecular targets. Often, aptamers bound with a stronger affinity to their respective ligand than to a complementary oligonucleotide sequence. This phenomenon was exploited to control the oligonucleotide hybridization mediated fusion described above by the presence of the appropriate ligand.

Figure 12:
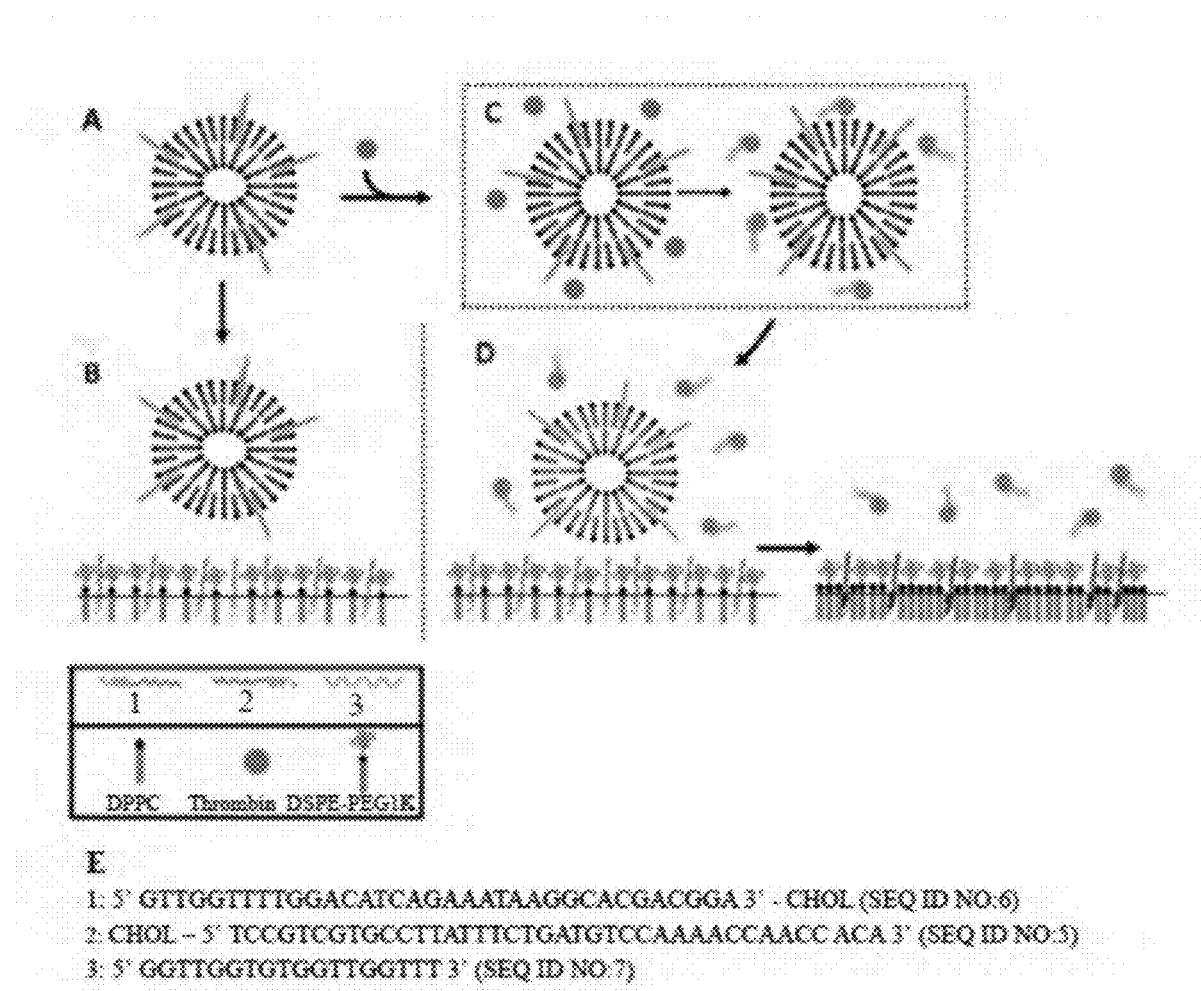
FIG. 12 is schematic illustration of aptamer-ligand binding mediated liposome fusion: DPPC (Panels A and E) liposomes were prepared with 5'chol-oligonucleotide and aptamer. Panel B is an illustration showing when these liposomes are added to a DSPE-PEG1k/3'chol-oligonucleotide laden LC interface fusion is inhibited since the aptamer blocks oligonucleotide hybridization. Panels C and D is an illustration showing that if the liposomes are mixed prior to thrombin addition, it becomes bound to the aptamer causing it to disassociate from 5'chol-oligonucleotide and allow oligonucleotide hybridization mediated fusion to proceed. Panel E shows oligonucleotide sequences used.

The detection scheme is schematically illustrated in FIG. 12. Liposomes were prepared with 5'chol-oligonucleotide and exposed to a complementary aptamer sequence that bound to the protein thrombin. In the absence of thrombin the aptamer was hybridized to 5'chol-oligonucleotide (FIG. 12, panel a), and effectively blocked hybridization between the liposomes and surface-anchored oligonucleotide strands. However, when liposomes were exposed to sufficiently high concentrations of thrombin (FIG. 12, panel b), the aptamer was expected to dissociate from 5'chol-oligonucleotide due to competitive binding with thrombin, freeing the liposome-anchored 5'chol-oligonucleotide to hybridize with surface anchored 3'chol-oligonucleotide (FIG. 12, panel c) and promoting fusion. Thus, it is believed that the exposure of liposomes prepared with 5'chol-oligonucleotide and aptamer to a DSPE-PEG 3'chol-oligonucleotide laden interface would fail to induce a transition to homeotropic orientation. But such a transition was expected to occur in the presence of thrombin.

Figure 13:
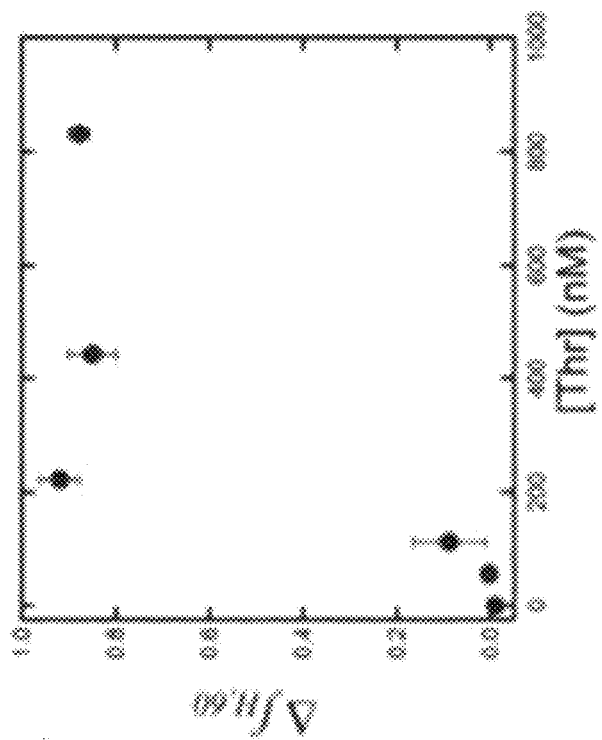
FIG. 13 shows data for thrombin dose-response. Panel A shows the fractional increase in homeotropic area ($f_H$) observed when adding DPPC/5'chol-oligonucleotide/aptamer liposomes a priori incubated with varying concentrations of thrombin to a DSPE-PEG1k/3'chol-oligonucleotide laden interface. Panel B shows the fractional increase in homeotropic area 60 minutes after the introduction of liposomes ($f_{H,60}$) plotted against thrombin concentration. [DPPC]≈1.36 mM; [5'chol-oligonucleotide]≈[aptamer]≈ 0.85 µM; $D_{pore}$=100 nm.
Figure 13:
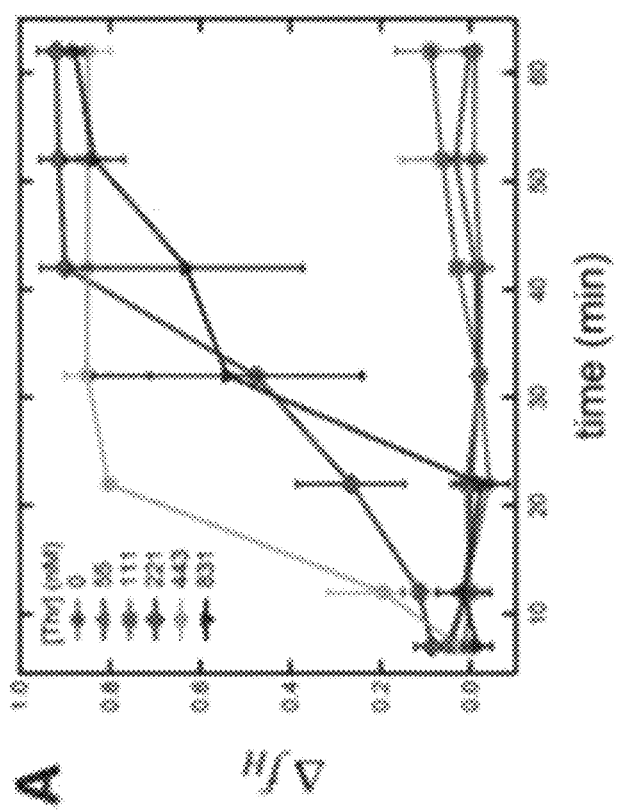

FIG. 13 summarizes the results of experiments testing these hypotheses as a function of thrombin concentration. Specifically, a transition to homeotropic orientation was observed only when DPPC/5'chol-oligonucleotide/aptamer liposomes were added to a DSPE-PEG1k/3'chol-oligonucleotide laden aqueous/LC interface in the presence of sufficiently high concentrations of thrombin. When the thrombin concentration was less than ~110 nM, no increase in homeotropic coverage was observed after ~60 min, while at concentrations in the range 221-831 nM a transition to nearly 100% homeotropic coverage was observed. Assuming a simple competitive binding model with disassociation constants of 200 nM and 196 nM for aptamer-thrombin and aptamer-oligonucleotide binding respectively, it was calculated that ~14° of the aptamer was bound to thrombin at [thrombin]≈220 nM. This correlates with ~44% of the 5'chol-oligonucleotide being free to undergo hybridization with surface anchored oligonucleotide, providing some insight into the fundamental sensitivity of the system. Dose-response measurements were taken for up to ~1 h after addition of liposomes and no increase in homeotropic coverage was observed at low thrombin concentrations. However, when monitoring this system for longer times (>4 hrs) a slow transition to homeotropic was observed even in the absence of thrombin. It is believed that this behavior was due to the dynamic behavior of oligonucleotide duplexes, in particular to the fact that the aptamer and 5'chol-oligonucleotide existed in dynamic equilibrium. Thus, for short periods of time, and at relatively low probability, the 5'chol-oligonucleotide may have been unblocked by aptamer, creating a small but finite probability for 5'chol-oligonucleotide/3'chol-oligonucleotide hybridization. The cumulative effect of these low probability events were observed because once they occurred, they were essentially irreversible since the lipids used in our study had an effectively insurmountable energy barrier to desorption. However, the rate of these "false negative" events was sufficiently low to monitor the specific fusogenic activity mediated by aptamer-ligand binding.

CONCLUSIONS

While LC interfaces have previously been designed to detect specific proteins, prior to the discovery by the present inventors a robust detection scheme that combines protein resistant surfaces with protein recognition-mediated LC orientational transformations has not been realized. Previous studies have shown that macromolecular proteins readily adsorbed to the aqueous/LC interface, disrupted the interfacial structure associated with homeotropic orientation, and inhibited specific protein detection. Oligo-ethylene glycol laden aqueous/LC interfaces reduced non-specific protein adsorption, consequently inhibiting the proteins' ability to disrupt the homeotropic orientation associated with surfactant laden interfaces. Here, the present inventors employed similar interfacial conditions to create protein-resistant surfaces within a robust detection scheme. To illustrate this point, the present inventors showed that when thrombin was added during DPPC liposome fusion, protein adsorption to the interface inhibited the extent to which DPPC was able to induce a transition to homeotropic orientation (FIG. 15). Thus, in detection scheme of the present invention, if the surfaces had no resistance to non-specific protein adsorption, it would not have been possible to observe a transition to homeotropic orientation. The observation of nearly 100% homeotropic coverage, even in the presence of relatively high concentrations of thrombin (FIG. 13, panel a), was evidence of interfacial conditions that not only inhibited spontaneous liposome fusion but also inhibited the non-specific adsorption of proteins. While decreased fusion kinetics were observed at thrombin concentrations >800 nM (likely due to thrombin interfering with the fusion dynamics), a complete transition was still observed, suggesting that the PEG sufficiently inhibited non-specific protein adsorption even at high thrombin concentrations. Thus, the present inventors have discovered and shown herein that oligonucleotide hybridization mediated fusion at protein resistant surfaces was exploited for detection of macromolecular proteins. Since the materials required for these experiments were relatively inexpensive (requiring only a simple optical set-up) and responded rapidly ($t_{50\%}$<1 min), this approach can be readily used for high throughput screening of fusogenic receptors and aptamer-based biosensing. This approach can be extended to detecting other types of receptor mediated liposome fusion (e.g., SNARE, small molecule) and further optimizing conditions (e.g., PEG size, oligonucleotide:aptamer ratio) for advanced aptamer based bio-sensing applications (e.g., detection in complex media).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

SEQUENCE LISTING

<110> The Regents of the University of Colorado, a body corporate
<120> BINDING DETECTION USING LIQUID CRYSTAL
<130> CU-007600US
<140> Ser. No. 15/121,750
<141> 2016 Aug. 25
<150> PCT/US15/21609
<151> 2015 Mar. 19
<150> 61/955,592
<151> 2014 Mar. 19
<160> 7
<170> PatentIn version 3.5
<210> 1
<211> 27
<212> DNA
<213> Artificial Sequence
<220>
<223> ssDNA Adenosine Selective Aptamer
<400> 1
acctggggga gtattgcgga ggaaggt 27
<210> 2
<211> 27
<212> DNA
<213> Artificial Sequence
<220>
<223> ssDNA mismatch adenosine aptamer where one nucleobase of Adenosine Selective Aptamer is substituted with a different nucleobase
<400> 2
acctggggga gtattgcgga gcaaggt 27
<210> 3
<211> 44
<212> RNA
<213> Artificial Sequence
<220>
<223> ssRNA arginine selective aptamer
<400> 3
gacgagaagg agcgcugguu cuacuagcag guaggucacu cguc 44
<210> 4
<211> 27
<212> DNA
<213> Artificial Sequence
<220>
<223> FRET pair labeled adenosine selective aptamer
<220>
<221> misc_feature
<222> (1) . . . (1)
<223> Linked to FAM (Fluorescein amidite)
<220>
<221> misc_feature
<222> (27) . . . (27)
<223> Linked to TAMRA (Carboxytetramethylrhodamine)
<400> 4
acctggggga gtattgcgga ggaaggt 27
<210> 5
<211> 39
<212> DNA
<213> Artificial Sequence
<220>
<223> Oligonucleotide having cholesterol attached at 5'-end
<220>
<221> misc_feature
<222> (1) . . . (1)
<223> Cholesterol linked 5'-end
<400> 5
tccgtcgtgc cttatttctg atgtccaaaa ccaaccaca 39
<210> 6
<211> 35
<212> DNA
<213> Artificial Sequence
<220>
<223> Oligonucleotide with cholesterol at 3'-end
<220>
<221> misc_feature
<222> (35) . . . (35)
<223> Cholesterol linked at 3'-end
<400> 6
gttggttttg gacatcagaa ataaggcacg acgga 35
<210> 7
<211> 18
<212> DNA
<213> Artificial Sequence
<220>
<223> Aptamer
<400> 7
ggttggtgtg gttgttt 18

SEQUENCE LISTING

<160> NUMBER OF SEQ ID NOS: 7

<210> SEQ ID NO 1
<211> LENGTH: 27
<212> TYPE: DNA
<213> ORGANISM: Artificial Sequence
<220> FEATURE:
<223> OTHER INFORMATION: ssDNA Adenosine Selective Aptamer

<400> SEQUENCE: 1
acctggggga gtattgcgga ggaaggt                                          27

<210> SEQ ID NO 2
<211> LENGTH: 27
<212> TYPE: DNA
<213> ORGANISM: Artificial Sequence
<220> FEATURE:
<223> OTHER INFORMATION: ssDNA mismatch adenosine aptamer where one
      nucleobase of Adenosine Selective Aptamer is substituted with a
      different nucleobase

<400> SEQUENCE: 2
acctggggga gtattgcgga gcaaggt                                          27

<210> SEQ ID NO 3
<211> LENGTH: 44
<212> TYPE: RNA
<213> ORGANISM: Artificial Sequence
<220> FEATURE:
<223> OTHER INFORMATION: ssRNA arginine selective aptamer

<400> SEQUENCE: 3
gacgagaagg agcgcugguu cuacuagcag guaggucacu cguc                       44

<210> SEQ ID NO 4
<211> LENGTH: 27
<212> TYPE: DNA
<213> ORGANISM: Artificial Sequence
<220> FEATURE:
<223> OTHER INFORMATION: FRET pair labeled adenosine selective aptamer
<220> FEATURE:
<221> NAME/KEY: misc_feature
<222> LOCATION: (1)..(1)
<223> OTHER INFORMATION: Linked to FAM (Fluorescein amidite)
<220> FEATURE:
<221> NAME/KEY: misc_feature
<222> LOCATION: (27)..(27)
<223> OTHER INFORMATION: Linked to TAMRA (Carboxytetramethylrhodamine)

<400> SEQUENCE: 4
acctggggga gtattgcgga ggaaggt                                          27

<210> SEQ ID NO 5
<211> LENGTH: 39
<212> TYPE: DNA
<213> ORGANISM: Artificial Sequence
<220> FEATURE:
<223> OTHER INFORMATION: Oligonucleotide having cholesterol attached at
      5'-end
<220> FEATURE:
<221> NAME/KEY: misc_feature
<222> LOCATION: (1)..(1)
<223> OTHER INFORMATION: Cholesterol linked 5'-end

<400> SEQUENCE: 5
tccgtcgtgc cttatttctg atgtccaaaa ccaaccaca                             39

<210> SEQ ID NO 6

```
<211> LENGTH: 35
<212> TYPE: DNA
<213> ORGANISM: Artificial Sequence
<220> FEATURE:
<223> OTHER INFORMATION: Oligonucleotide with cholesterol at 3'-end
<220> FEATURE:
<221> NAME/KEY: misc_feature
<222> LOCATION: (35)..(35)
<223> OTHER INFORMATION: Cholesterol linked at 3'-end

<400> SEQUENCE: 6
gttggttttg gacatcagaa ataaggcacg acgga                              35

<210> SEQ ID NO 7
<211> LENGTH: 18
<212> TYPE: DNA
<213> ORGANISM: Artificial Sequence
<220> FEATURE:
<223> OTHER INFORMATION: Aptamer

<400> SEQUENCE: 7
ggttggtgtg gttggttt                                                 18
```

What is claimed is:

1. A method for determining the presence of a ligand that is not labeled in a sample fluid, said method comprising:

(a) contacting said sample fluid with a surfactant-nucleic acid aptamer interfacial layer under conditions sufficient to form a nucleic acid aptamer-ligand complex in a non-hybridization manner when said ligand is present in said sample fluid, wherein said surfactant-aptamer interfacial layer is present at a liquid crystal and a polar solvent interface, and wherein said nucleic acid aptamer is capable of selectively binding to said ligand, and wherein said nucleic acid aptamer-ligand complex changes orientation of said liquid crystal compared to the orientation of said liquid-crystal in the absence of said nucleic acid aptamer-ligand complex; and (b) detecting the orientation of said liquid crystal, wherein detection of change in orientation of said liquid crystal indicates the presence of said ligand in said sample fluid.

2. The method of claim 1, wherein said surfactant comprises a cationic surfactant.

3. The method of claim 1, wherein said cationic surfactant comprises a monoalkylquaternary ammonium surfactant, dialkylquaternary ammonium surfactant, trialkylquaternary ammonium surfactant, a monoalkylpyridinium surfactants, quaternized polyoxyethylenated long chain amines, or a combination thereof.

4. The method of claim 1, wherein said surfactant further comprises a nonionic surfactant.

5. The method of claim 4, wherein said nonionic surfactant comprises an alkylpolyoxyethylene surfactant, a polyoxyethylenated polyoxypropylene, sorbitan alkyl ester, a polyoxyethylene glycol sorbitan alkyl ester surfactant, or a mixture thereof.

6. The method of claim 1, wherein said liquid crystal is a thermotropic liquid crystal.

7. The method of claim 6, wherein said liquid crystal comprises 4-cyano-4'-pentylbiphenyl, 4-cyano-4'-pentyl-p-terphenyl, N-(4-methoxybenzylidene)-4'-butylaniline, 4'-di-n-hexyldiphenyldiacetylene, other biphenyl or terphenyl liquid crystal compounds, or a mixture thereof.

8. The method of claim 1, wherein said polar solvent comprises an aqueous solution.

9. The method of claim 1, wherein said step of detecting orientation of said liquid crystal comprises detecting a change in the birefringence of said liquid crystal.

10. The method of claim 1, wherein polarized light is used to detect orientation of said liquid crystal.

11. The method of claim 1, where light microscopy is used to detect orientation of said liquid crystal.

12. A method for detecting the presence of a non-labeled ligand in a sample using a non-labeled nucleic acid aptamer, said method comprising:

placing said sample on a ligand detection apparatus comprising a liquid crystal, a surfactant, a polar solvent, and a non-labeled nucleic acid aptamer that binds selectively to said ligand in a non-hybridization manner, wherein a surfactant-nucleic acid aptamer interfacial layer is present at the interface of said liquid crystal and said polar solvent, and wherein said nucleic acid aptamer changes conformation upon binding to said ligand, and wherein the orientation of said liquid crystal changes depending on the conformation of said nucleic acid aptamer; and detecting the change in orientation of said liquid crystal to determine the presence of said ligand in said sample.

13. The method of claim 12, wherein said ligand detection apparatus further comprises a solid substrate, and wherein said liquid crystal is bound to said solid substrate.

14. The method of claim 12, wherein said method of detecting the change in orientation of said liquid crystal comprises determining a change in birefringence of said liquid crystal.

* * * * *